United States Patent
Englert et al.

[11] Patent Number: 5,977,177
[45] Date of Patent: Nov. 2, 1999

[54] SUBSTITUTED BENZENESULFONYLUREAS AND-THIOUREAS, PROCESSES FOR THEIR PREPARATION AND USE OF PHARMACEUTICAL PREPARATIONS BASED ON THESE COMPOUNDS, AND MEDICAMENTS CONTAINING THEM

[75] Inventors: Heinrich Englert, Hofheim; Uwe Gerlach, Hattersheim; Dieter Mania, Königstein; Heinz Gögelein; Joachim Kaiser, both of Frankfurt, all of Germany

[73] Assignee: Hoechst Aktiengesellschaft, Frankfurt am Main, Germany

[21] Appl. No.: 09/090,403

[22] Filed: Jun. 4, 1998

Related U.S. Application Data

[62] Division of application No. 08/602,018, Feb. 15, 1996, Pat. No. 5,880,155.

[30] Foreign Application Priority Data

Feb. 17, 1995 [DE] Germany .......................... 195 05 398
Jun. 23, 1995 [DE] Germany .......................... 195 22 920

[51] Int. Cl.⁶ ........................ A61K 31/175; C07C 311/16
[52] U.S. Cl. .................. 514/592; 514/227.5; 514/237.5; 514/255; 514/330; 514/586; 514/585; 514/593; 514/821; 544/59; 544/168; 544/386; 546/226; 564/23; 564/25; 564/40; 564/64; 564/42
[58] Field of Search ..................................... 514/586, 585, 514/592, 593, 821, 227.5, 237.5, 255, 330; 564/23, 39, 40, 41, 42; 544/59, 168, 386; 546/226

[56] References Cited

U.S. PATENT DOCUMENTS 3,336,322 8/1967 Weber .
3,426,067 2/1969 Weber .

FOREIGN PATENT DOCUMENTS 0 612 724  8/1994  European Pat. Off. .
1 198 354  8/1965  Germany .
1 939 895  2/1971  Germany .

OTHER PUBLICATIONS

Derwent Abstract of DE 1 939 895. 1971.
Derwent Abstract of EP 0 612 724. 1994.

*Primary Examiner*—Shailendra Kumar
*Attorney, Agent, or Firm*—Finnegan, Henderson, Farabow, Garrett & Dunner, L.L.P.

[57] ABSTRACT

This invention relates to substituted benzenesulfonylureas and -thioureas, processes for their preparation and use of pharmaceutical preparations based on these compounds, and medicaments containing them.

Substituted benzenesulfonylureas and -thioureas of the formula I

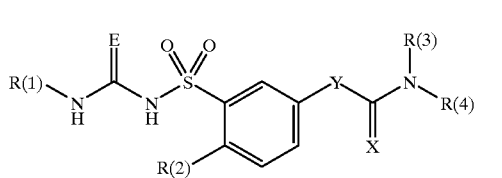

exhibit effects on the cardiovascular system.

14 Claims, No Drawings

SUBSTITUTED BENZENESULFONYLUREAS AND -THIOUREAS, PROCESSES FOR THEIR PREPARATION AND USE OF PHARMACEUTICAL PREPARATIONS BASED ON THESE COMPOUNDS, AND MEDICAMENTS CONTAINING THEM

This is a division of application Ser. No. 08/602,018, filed Feb. 15, 1996 now U.S. Pat. No. 5,880,155.

DESCRIPTION

This invention relates to substituted benzenesulfonylureas and -thioureas, processes for their preparation and use of pharmaceutical preparations based on these compounds, and medicaments containing them.

The invention relates to substituted benzenesulfonylureas and -thioureas I

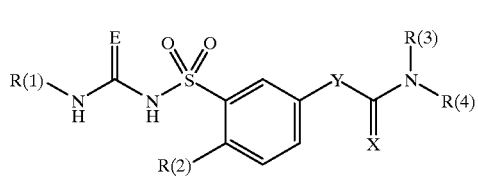

in which:
- R(1) is hydrogen, fluorine, chlorine, alkyl having 1, 2, 3, 4, 5, 6 or 7 carbon atoms or cycloalkyl having 3, 4, 5, 6 or 7 carbon atoms;
- R(2) is hydrogen, alkyl having 1, 2, 3, 4, 5 or 6 carbon atoms, alkoxy having 1, 2, 3, 4, 5 or 6 carbon atoms, fluoroalkoxy having 1, 2, 3, 4, 5 or 6 carbon atoms, mercaptoalkyl having 1, 2, 3, 4, 5 or 6 carbon atoms, cycloalkyl having 3, 4, 5 or 6 carbon atoms, additionally ($C_1$–$C_8$) chains in which n carbon atoms are replaced by heteroatoms, e.g. O, N or S, (where n=1–4), F or Cl;
- R(3) is H, alkyl having 1, 2, 3, 4, 5, 6, 7, 8, 9, 10, 11 or 12 carbon atoms, cycloalkyl having 3, 4, 5, 6, 7, 8, 9 or 10 carbon atoms, fluoroalkyl having 1, 2, 3, 4, 5 or 6 carbon atoms, fluorocycloalkyl having 3, 4, 5 or 6 carbon atoms, or ($C_1$–$C_{10}$) chains in which n carbon atoms are replaced by heteroatoms, e.g. O, N or S (n=1, 2, 3 or 4);
- R(4) is hydrogen, alkyl having 1, 2, 3, 4, 5, 6, 7, 8, 9, 10, 11 or 12 carbon atoms, cycloalkyl having 3, 4, 5, 6, 7, 8, 9 or 10 carbon atoms, fluoroalkyl having 1, 2, 3, 4, 5 or 6 carbon atoms, fluorocycloalkyl having 3, 4, 5 or 6 carbon atoms, or ($C_1$–$C_{10}$) chains in which n carbon atoms are replaced by heteroatoms, e.g. O, N or S (n=1, 2, 3 or 4); or
- R(3) and R(4) together form a $(CH_2)_{2-8}$ ring, in which one or more of the $CH_2$ groups can be replaced by heteroatoms;
- R(3) and R(4) can be identical or different;
- E is oxygen or sulfur;
- X is oxygen or sulfur;
- Y is $[CR(5)R(5')]_m$;
  - R(5) and R(5') independently of one another are hydrogen or alkyl having 1 or 2 carbon atoms; where the members [CR(5)R(5')] are identical or different;
  - m is 1, 2, 3 or 4;

and their pharmaceutically tolerable salts.

The term alkyl describes, if not stated otherwise, straight-chain or branched saturated hydrocarbon radicals. The cycloalkyl radical can additionally carry an alkyl substituent. Halogen substituents which can be employed are the elements fluorine, chlorine, bromine and iodine. Furthermore, compounds having centers of chirality in the alkyl chains Y, R(3) and R(4) can occur. In this case, the invention includes both the individual antipodes per se, and a mixture of the two enantiomers in different proportions, and also the associated meso compounds or mixtures of meso compounds, the enantiomers or diastereomers.

Similar sulfonylureas are disclosed in German Offenlegungsschrift 1 198 354. The hypoglycemic actions of the sulfonylureas are described therein. A prototype of such hypoglycemic sulfonylureas is glibenclamide, which is used therapeutically as an agent for the treatment of diabetes mellitus and serves in research as a much-esteemed tool for the study of so-called ATP-sensitive potassium channels. In addition to its hypoglycemic action, glibenclamide has still other actions, which up to now can still not be employed therapeutically, but which all are attributed to blockade of exactly these ATP-sensitive potassium channels. This includes, in particular, an antifibrillatory action on the heart. In the treatments of ventricular fibrillation or its preliminary stages, however, a simultaneous blood sugar fall would be undesirable or even dangerous, as it can further aggravate the condition of the patient.

It was therefore the object of the present invention to synthesize compounds which have a cardiac action which is equally as good as glibenclamide but do not affect the blood sugar or affect it distinctly less in cardioactive doses or concentrations than glibenclamide.

Suitable experimental animals for the detection of such actions are, for example, mice, rats, guinea-pigs, rabbits, dogs, monkeys or pigs.

The compounds I are used as pharmaceutical active compounds in human and veterinary medicine. They can further be used as intermediates for the production of further pharmaceutical active compounds.

Preferred compounds I are those in which:
- R(1) is hydrogen, alkyl having 1, 2, 3, 4, 5, 6 or 7 carbon atoms or cycloalkyl having 3, 4, 5, 6 or 7 carbon atoms;
- R(2) is hydrogen, F, Cl, alkyl having 1, 2, 3, 4, 5 or 6 carbon atoms, alkoxy having 1, 2, 3, 4, 5 or 6 carbon atoms, fluoroalkoxy having 1, 2, 3, 4, 5 or 6 carbon atoms, mercaptoalkyl having 1, 2, 3, 4, 5 or 6 carbon atoms, cycloalkyl having 3, 4, 5 or 6 carbon atoms, a $(CH_2)_{2-7}$ chain in which one or more of the $CH_2$ groups can be replaced by heteroatoms O, N or S;
- R(3) and R(4) are identical or different and are hydrogen, alkyl having 1, 2, 3, 4, 5, 6, 7, 8, 9, 10, 11 or 12 carbon atoms, cycloalkyl having 3, 4, 5, 6, 7, 8, 9 or 10 carbon atoms, fluoroalkyl having 1, 2, 3, 4, 5 or 6 carbon atoms, fluorocycloalkyl having 3, 4, 5 or 6 carbon atoms, or a ($C_1$–$C_{10}$) chain in which one or more of the $CH_2$ groups can be replaced by heteroatoms O, S or N; or
- R(3) and R(4) together are $(CH_2)_{2-8}$, in which one of the $CH_2$ groups can be replaced by a heteroatom O, S or N;
- E is oxygen or sulfur;
- X is oxygen or sulfur;
- Y is $[CR(5)R(5')]_m$;
  - m is 1, 2, 3 or 4;
  - R(5) and R(5') independently of one another are hydrogen or alkyl having 1 or 2 carbon atoms; where the members [CR(5)R(5')] are identical or different;

and their pharmaceutically tolerable salts.

Particularly preferred compounds of the formula I are those in which:

R(1) is hydrogen, alkyl having 1, 2, 3 or 4 carbon atoms, or cycloalkyl having 3, 4, 5, 6 or 7 carbon atoms;

R(2) is F, Cl, alkyl having 1, 2, 3 or 4 carbon atoms, alkoxy having 1, 2, 3 or 4 carbon atoms or a $(CH_2)_{2-7}$ chain, in which one or more of the $CH_2$ groups can be replaced by heteroatoms O, S or N;

R(3) and R(4) are identical or different and are hydrogen, alkyl having 1, 2, 3, 4, 5, 6, 7, 8, 9 or 10 carbon atoms, cycloalkyl having 3, 4, 5 or 6 carbon atoms, or $(CH_2)_{1-10}$, in which one or more $CH_2$ groups can be replaced by heteroatoms O, S or N; or R(3) and R(4) groups together $(CH_2)_{2-7}$, in which one of the $CH_2$ groups can be replaced by heteroatoms O, S or N;

E is oxygen or sulfur;

X is oxygen or sulfur;

Y is $[CR(5)R(5')]_m$;

R(5) and R(5') independently of one another are hydrogen or alkyl having 1 or 2 carbon atoms; where the members [CR(5)R(5')] are identical or different m is 1, 2, 3 or 4;

and their pharmaceutically tolerable salts.

Very particularly preferred are those compounds I in which:

R(1) is hydrogen, alkyl having 1, 2, 3 or 4 carbon atoms, or cycloalkyl having 3 or 4 carbon atoms;

R(2) is methoxy or ethoxy;

R(3) and R(4) are identical or different and are hydrogen, alkyl having 4, 5, 6, 7 or 8 carbon atoms, cycloalkyl having 3, 4, 5 or 6 carbon atoms or a $(C_{3-8}H_{7-17})$ group, in which one or more of the $CH_2$ groups can be replaced by heteroatoms O, S or N; or R(3) and R(4) together are the $(CH_2)_{2-8}$, group, in which one of the $CH_2$ groups can be replaced by heteroatoms O, S or N;

E is sulfur or oxygen;

X is oxygen;

Y is $[CR(5)R(5')]_m$;

R(5) and R(5') independently of one another are hydrogen or alkyl having 1 or 2 carbon atoms; where the members [CR(5)R(5')] are identical or different;

m is 1 or 2;

and their pharmaceutically tolerable salts.

Likewise very particularly preferred compounds I are those in which:

R(1) is hydrogen, alkyl having 1, 2 or 3 carbon atoms or cycloalkyl having 3 carbon atoms;

R(2) is methoxy or ethoxy;

R(3) and R(4) are identical or different and are hydrogen, alkyl having 5, 6, 7 or 8 carbon atoms, cycloalkyl having 5 or 6 carbon atoms or a $[C_{5-8}H_{11-17}]$ group, in which one or more of the $CH_2$ groups can be replaced by heteroatoms O, S or N; or R(3) and R(4) together are $(CH_2)_{5-8}$, in which one of the $CH_2$ groups can be replaced by heteroatoms O, S or N;

E is oxgyen or sulfur;

X is oxygen;

Y is $[CR(5)R(5')]_m$;

R(5) and R(5') independently of one another are hydrogen or alkyl having 1 or 2 carbon atoms; where the members [CR(5)R(5')] are identical or different;

m is 1 or 2;

and their pharmaceutically tolerable salts.

Additionally very particularly preferred compounds I are those in which:

R(1) is hydrogen, alkyl having 1, 2 or 3 carbon atoms or cycloalkyl having 3 carbon atoms;

R(2) is methoxy or ethoxy;

R(3) is hydrogen;

R(4) is alkyl having 5, 6, 7 or 8 carbon atoms, cycloalkyl having 5 or 6 carbon atoms or a $(C_{5-8}H_{11-17})$ group, in which one or more of the $CH_2$ groups can be replaced by heteroatoms O, S or N;

E is sulfur or oxygen;

X is oxygen;

Y is $[CR(5)R(5')]_m$;

R(5) and R(5') independently of one another are hydrogen methyl; where the members [CR(5)R(5')] are identical or different;

m is 1 or 2;

and their pharmaceutically tolerable salts.

The compounds I of the present invention are useful pharmaceuticals for the treatment of cardiac arrhythmias of all types of origin and for the prevention of sudden heart death due to arrhythmia and can therefore be used as antiarrhythmics. Examples of arrhythmic disorders of the heart are supraventricular arrhythmias, such as atrial tachycardias, atrial flutters or paroxysmal supraventricular arrhythmias or ventricular arrhythmias, such as ventricular extrasystoles, but in particular life-threatening ventricular tachycardias or the particularly dangerous ventricular fibrillation. They are suitable, in particular, for those cases where arrhythmias are the consequence of a constriction of a coronary vessel, such as occur in angina pectoris or during an acute cardiac infarct or as a chronic consequence of a cardiac infarct. They are therefore particularly suitable in postinfarct patients for the prevention of sudden heart death. Further syndromes where arrhythmias of this type and/or sudden heart death due to arrhythmia play a part are, for example, cardiac insufficiency or cardiac hypertrophy as a consequence of a chronically increased blood pressure.

Moreover, the compounds I can positively affect a decreased contractility of the heart. This can include a disease-related Fall in cardiac contractility, for example in cardiac insufficiency, but also acute cases such as heart failure in the case of the effects of shock. Likewise, in the case of a heart transplantation, after operation has taken place the heart can resume its operational capacity more rapidly and reliably. The same applies to operations on the heart, which necessitate a temporary stopping of cardiac activity by means of cardioplegic solutions, it being possible to use the compounds both for the protection of the organs, for example during treatment with or storage thereof in physiological bath fluids, and during transfer to the recipient body.

The invention furthermore relates to processes for the preparation of the compounds I. A procedure can thus be used which comprises (a) reacting a sulfonamide of the formula II

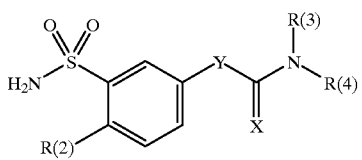

or its salt of the formula III

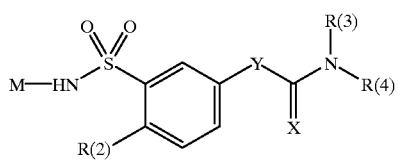

with an R(1)-substituted isocyanate of the formula IV

R(1)—N=C=O    IV in which R(1), R(2), R(3), R(4), X, Y and M have the meanings indicated in claim 1, to give the substituted benzenesulfonylurea Ia.

Suitable cations M in the salts of the formula III are alkali metal and alkaline earth metal ions. Equivalently to the R(1)-substituted isocyanates IV, R(1)-substituted carbamic acid esters, R(1)-substituted carbamoyl halides or R(1)-substituted ureas can be employed.

(b) A benzenesulfonylurea of the formula Ia

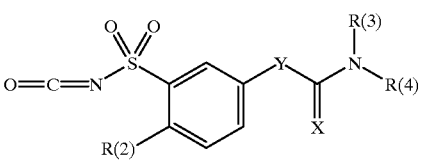

can be prepared from an aromatic benzenesulfonamide of the formula II or its salt III with an R(1)-substituted trichloroacetamide of the formula V Cl₃C—(C=O)NH—R(1)

in the presence of a base in an inert solvent according to Synthesis 1987, 734–735 at temperatures from 25° C. to 150° C.

Suitable bases are, for example, alkali metal or alkaline earth metal hydroxides, or alternatively alkoxides, such as sodium hydroxide, potassium hydroxide, calcium hydroxide, sodium methoxide, sodium ethoxide, potassium methoxide or potassium ethoxide. Suitable inert solvents are ethers such as tetrahydrofuran, dioxane, ethylene glycol dimethyl ether (diglyme), nitriles such as acetonitrile, amides such as dimethylformamide (DMF) or N-methylpyrrolidone (NMP), hexamethylphosphoramide, sulfoxides such as DMSO, sulfones such as sulfolane, hydrocarbons such as benzene, toluene, xylenes. Furthermore, mixtures of these solvents with one another are also suitable.

(c) A benzenesulfonylthiourea Ib

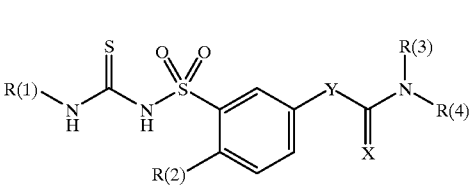

is prepared from a benzenesulfonamide II or its salt III and an R(1)-substituted isothiocyanate VI

R(1)—N=C=S.    VI (d) A benzenesulfonylurea of the formula I a can be prepared by a conversion reaction of a benzenesulfonylthiourea of the formula Ib. The replacement of the sulfur atom by an oxygen atom in the appropriately substituted benzenesulfonylthiourea Ib can be carried out, for example, with the aid of oxides or salts of heavy metals or also by use of oxidants such as hydrogen peroxide, sodium peroxide or nitrous acid. Thioureas can also be desulfurized by treatment with phosgene or phosphorus pentachloride. The intermediate compounds obtained are chloroformamidines or carbodiimides, which are converted into the corresponding substituted benzenesulfonylureas Ia, for example by hydrolysis or addition of water. During desulfurization, isothioureas behave like thioureas and can accordingly also be used as starting substances for these reactions.

(e) A benzenesulfonylurea Ia can be prepared by reaction of an amine of the formula R(1)—NH₂ with a benzenesulfonyl isocyanate of the formula VII

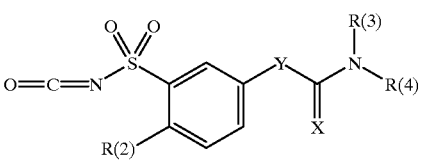

Likewise, an amine R(1)—NH₂ can be reacted with a benzenesulfonylcarbamic acid ester, a -carbamoyl halide or a benzenesulfonylurea Ia [where R(1)=H] to give a compound I.

(f) A benzenesulfonylthiourea Ib can be prepared by reaction of an amine of the formula R(1)—NH₂ with a benzenesulfonyl isothiocyanate of the formula VIII

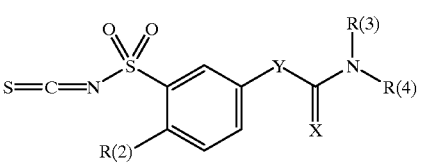

(g) A benzenesulfonylurea Ia can be prepared from a benzenesulfonylurea of the formula IX IX
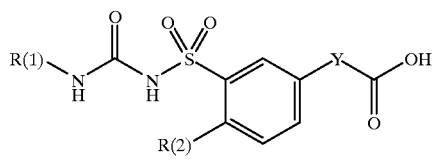

and R(3)R(4)NH by means of dehydrating agents or activation by means of carbonyl halides or formation of mixed anhydrides. The dehydrating agents employed can be all compounds suitable for the preparation of amide bonds, such as dicyclohexylcarbodiimide, carbonyldiimidazole or propanephosphoric anhydride. The solvents used are inert nonprotic solvents such as THF, DMF, diethyl ether, dichloromethane, as well as mixtures of these solvents.

(h) A benzenesulfonylthiourea Ib can be prepared from a benzenesulfonylthiourea of the formula X X
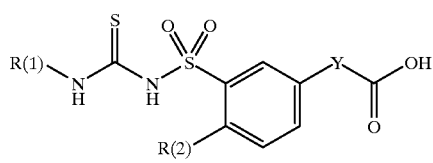

and R(3)R(4)NH by means of dehydrating agents or activation by means of carbonyl halides or formation of mixed anhydrides. The dehydrating agents employed can be all compounds suitable for the preparation of amide bonds, such as dicyclohexylcarbodiimide, carbonyldiimidazole or propanephosphoric ahydride. The solvents used are inert nonprotic solvents such as THF, DMF, diethyl ether, dichloromethane, as well as mixtures of these solvents.

The compounds I and their physiologically acceptable salts are useful therapeutics which are suitable not only as antiarrhythmics, but as prophylactics in disorders of the cardiovascular system, cardiac insufficiency, heart transplantation or cerebral vascular disorders in humans or mammals (for example monkeys, dogs, mice, rats, rabbits, guinea-pigs and cats).

Physiologically acceptable salts of the compounds I are understood according to Remmington's Pharmaceutical Science, 17th edition, 1985, pages 14–18 as meaning compounds of the formula XI, XI
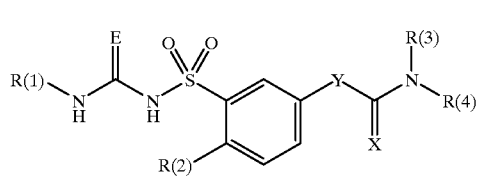

which can be prepared from nontoxic organic and inorganic bases and benzenesulfonylureas I.

Salts are preferred in this context in which M in the formula XI is a sodium, potassium, rubidium, calcium or magnesium ion, and also the acid addition products of basic amino acids, such as lysine or arginine.

The starting compounds for the mentioned synthesis processes of the benzenesulfonylureas I are prepared by methods known per se, as are described in the literature (for example in the standard works such as Houben-Weyl, Methoden der Organischen Chemie (Methods of Organic Chemistry), Georg Thieme Verlag, Stuttgart; Organic Reactions, John Wiley & Sons, Inc., New York; and also in the patent applications indicated above), namely under reaction conditions which are known and suitable for the reactions mentioned. In this case, use can also be made of variants which are known per se but not mentioned here in more detail. If desired, the starting substances can also be formed in situ in such a way that they are not isolated from the reaction mixture, but immediately reacted further.

A suitably substituted carboxylic acid of the formula XII can thus be subjected to a halosulfonation according to Scheme 1 and the sulfonamide XIII obtained by subsequent ammonolysis can be reacted with an appropriate amine R(3)R(4)NH after activation of the carboxylic acid group to give the carboxamide of the formula II.

Scheme 1

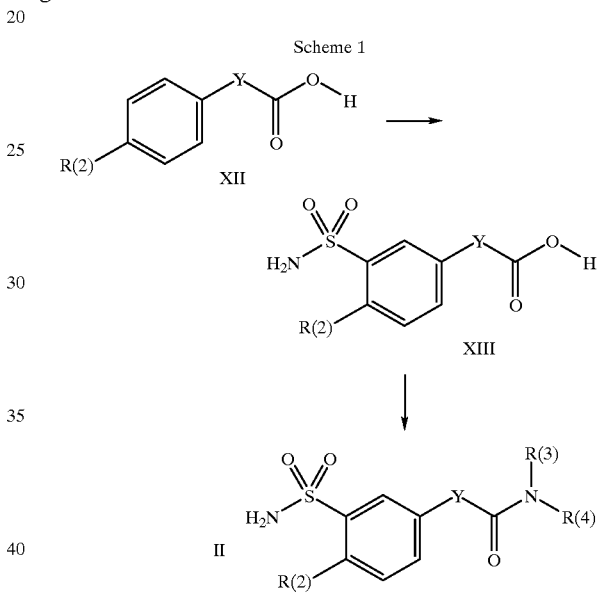

Suitable activation methods are the preparation of the carbonyl chloride or mixed carboxylic anhydrides using formyl halides. In addition, the reagents known for amide bond preparation, such as carbonyldiimidazole, dicyclohexylcarbodiimide and propanephosphoric anhydride, can be used.

The sulfonanides XIII

XIII
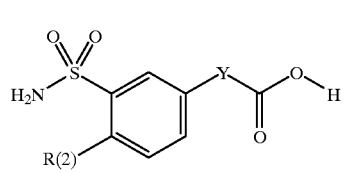

obtained in Scheme 1 as intermediates can be reacted with appropriate isocyanates of the formula

R(1)—N=C=X to give the benzenesulfonylureacarboxylic acids of the formula XIV

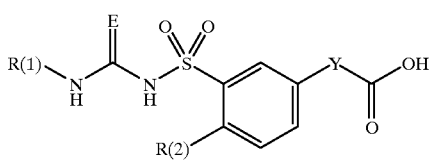

XIV

The compounds I can have one or more chiral centers. In their preparation they can therefore be obtained as racemates or, if optically active starting substances are used, alternatively in optically active form. If the compounds have two or more chiral centers, they can be obtained in the synthesis as mixtures of racemates from which the individual isomers can be isolated in pure form, for example by recrystallizing from inert solvents. If desired, racemates obtained can be separated into their enantiomers mechanically or chemically by methods known per se. Diastereomers can thus be formed from the racemates by reaction with an optically active resolving agent. Suitable resolving agents for basic compounds are, for example, optically active acids, such as the R- or R,R- and S- or S,S-forms of tartaric acid, dibenzoyltartaric acid, diacetyltartaric acid, camphorsulfonic acids, mandelic acids, malic acid or lactic acid. Carbinols can further be amidated with the aid of chiral acylating reagents, for example R- or S-α-methylbenzyl isocyanates, and then separated. The various forms of the diastereomers can be separated in a known morner, for example by fractional crystallization, and the enantiomers of the formula I can be liberated from the diastereomers in a known manner. Resolution of enantiomers is further carried out by chromatography on optically active support materials.

The compounds I according to the invention and their physiologically acceptable salts can be used for the production of pharmaceutical preparations. In this context, they can be brought into a suitable dose form together with at least one solid or liquid excipient or auxiliary on their own or in combination with other pharmaceuticals having cardiovascular activity, such as calcium antagonists, NO donors or ACE inhibitors. These preparations can be used as pharmaceuticals in human or veterinary medicine. Possible excipients are organic or inorganic substances which are suitable for enteral (for example oral) or parenteral administration, for example intravenous administration, or topical applications and do not react with the novel compounds, for example water, vegetable oils, benzyl alcohols, polyethylene glycols, glycerol triacetate, gelatin, carbohydrates such as lactose or starch, magnesium stearate, talc, lanolin and petroleum jelly. In particular, tablets, coated tablets, capsules, syrups, juices or drops are used for oral administration, solutions, preferably oily or aqueous solutions, and also suspensions, emulsions or implants, are used for rectal administration, and ointments, creams, pastes, lotions, gels, sprays, foams, aerosols, solutions (for example in alcohols such as ethanol or isopropanol, acetonitrile, 1,2-propanediol or their mixtures with one another or with water) or powders are used for topical application. The compounds I can also be lyophilized and the lyophilizates obtained used, for example, for the production of injection preparations. In particular for topical application, liposomal preparations are also suitable, which contain stabilizers and/or wetting agents, emulsifiers, salts and/or auxiliaries such as lubricants, preservatives, salts for affecting the osmotic pressure, buffer substances, colorants and flavorings and/or aromatic substances. If desired, they can also contain one or more further active compounds, for example one or more vitamins.

The doses which are necessary for the treatment of cardiac arrhythmias with the compounds I depend on whether the therapy is acute or prophylactic. Normally, a dose range of approximately at least 0.1 mg, preferably at least 1 mg, up to at most 100 mg, preferably up to at most 10 mg, per kg per day is adequate if prophylaxis is conducted. The dose can in this case be divided as an oral or parenteral individual dose or else in up to four individual doses. If acute cases of cardiac arrhythmias are treated, for example in an intensive care unit, parenteral administration can be advantageous. A preferred dose range in critical situations can then be 10 to 100 mg and be administered, for example, as an intravenous continuous infusion.

According to the invention, in addition to the compounds described in the working examples, the compounds I compiled in the following Table can also be obtained:

(1) 3-Sulfonylamino-N-methylaminocarbonyl-4-methoxyphenyl-N-methylacetamide
(2) 3-Sulfonylamino-N-methylaminocarbonyl-4-methoxyphenyl-N-ethylacetamide
(3) 3-Sulfonylamino-N-methylaminocarbonyl-4-methoxyphenyl-N-1-propylacetamide
(4) 3-Sulfonylamino-N-methylaminocarbonyl-4-methoxyphenyl-N-2-propylacetamide
(5) 3-Sulfonylamino-N-methylaminocarbonyl-4-methoxyphenyl-N-1-butylacetamide
(6) 3-Sulfonylamino-N-methylaminocarbonyl-4-methoxyphenyl-N-2-butylacetamide
(7) 3-Sulfonylamino-N-methylaminocarbonyl-4-methoxyphenyl-N-1-pentylacetamide
(8) 3-Sulfonylamino-N-methylaminocarbonyl-4-methoxyphenyl-N-2-pentylacetamide
(9) 3-Sulfonylamino-N-methylaminocarbonyl-4-methoxyphenyl-N-3-pentylacetamide
(10) 3-Sulfonylamino-N-methylaminocarbonyl-4-methoxyphenyl-N-1-butyl-2-methylacetamide
(11) 3-Sulfonylamino-N-methylaminocarbonyl-4-methoxyphenyl-N-1-butyl-3-methylacetamide
(12) 3-Sulfonylamino-N-methylaminocarbonyl-4-methoxyphenyl-N-1-hexylacetamide
(13) 3-Sulfonylamino-N-methylaminocarbonyl-4-methoxyphenyl-N-2-hexylacetamide
(14) 3-Sulfonylamino-N-methylaminocarbonyl-4-methoxyphenyl-N-3-hexylacetamide
(15) 3-Sulfonylamino-N-methylaminocarbonyl-4-methoxyphenyl-N-1-heptylacetamide
(16) 3-Sulfonylamino-N-methylaminocarbonyl-4-methoxyphenyl-N-2-heptylacetamide
(17) 3-Sulfonylamino-N-methylaminocarbonyl-4-methoxyphenyl-N-3-heptylacetamide
(18) 3-Sulfonylamino-N-methylaminocarbonyl-4-methoxyphenyl-N-1-octylacetamide
(19) 3-Sulfonylamino-N-methylaminocarbonyl-4-methoxyphenyl-N-2-octylacetamide
(20) 3-Sulfonylamino-N-methylaminocarbonyl-4-methoxyphenyl-N-1-adamantylacetarmide
(21) 3-Sulfonylamino-N-methylaminocarbonyl-4-methoxyphenyl-N-2-adamantylacetaide
(22) 3-Sulfonylamino-N-methylaminocarbonyl-4-methoxyphenyl-N-dimethylacetamide
(23) 3-Sulfonylamino-N-methylaminocarbonyl-4-methoxyphenyl-N-methyl-N'-ethylacetamide
(24) 3-Sulfonylamino-N-methylaminocarbonyl-4-methoxyphenyl-N-methyl-N'-1-propylacetamide
(25) 3-Sulfonylamino-N-methylaminocarbonyl-4-methoxyphenyl-N-methyl-N'-2-propylacetade

(26) 3-Sulfonylamino-N-methylaminocarbonyl-4-methoxyphenyl-N-methyl-N'-1-butylacetamide
(27) 3-Sulfonylamino-N-methylaminocarbonyl-4-methoxyphenyl-N-methyl-N'-2-butylacetamide
(28) 3-Sulfonylamino-N-methylaminocarbonyl-4-methoxyphenyl-N-diethylacetamide
(29) 3-Sulfonylamino-N-methylaminocarbonyl-4-methoxyphenyl-N-ethyl-N'-1-propylacetamide
(30) 3-Sulfonylamino-N-methylaminocarbonyl-4-methoxyphenyl-N-ethyl-N'-2-propylacetamide
(31) 3-Sulfonylamino-N-methylaminocarbonyl-4-methoxyphenylpyrrolidinylacetamide
(32) 3-Sulfonylamino-N-methylaminocarbonyl-4-methoxyphenylpiperidylacetamide
(33) 3-Sulfonylamino-N-methylaminocarbonyl-4-methoxyphenylmorpholinoacetamide
(34) 3-Sulfonylamino-N-methylaminocarbonyl-4-methoxyphenyl-N-methylpiperazinylacetamide
(35) 3-Sulfonylamino-N-methylaminocarbonyl-4-methoxyphenyl-4-thiomorpholinylacetamide
(36) 3-Sulfonylamino-N-methylaminothiocarbonyl-4-methoxyphenyl-N-methylacetamide
(37) 3-Sulfonylamino-N-methylaminothiocarbonyl-4-methoxyphenyl-N-ethylacetanmide
(38) 3-Sulfonylamino-N-methylaminothiocarbonyl-4-methoxyphenyl-N-1-propylacetamide
(39) 3-Sulfonylamino-N-methylaminothiocarbonyl-4-methoxyphenyl-N-2-propylacetamide
(40) 3-Sulfonylamino-N-methylaminothiocarbonyl-4-methoxyphenyl-N-1-butylacetamide
(41) 3-Sulfonylamino-N-methylaminothiocarbonyl-4-methoxyphenyl-N-2-butylacetamide
(42) 3-Sulfonylamino-N-methylaminothiocarbonyl-4-methoxyphenyl-N-1-pentylacetamide
(43) 3-Sulfonylamino-N-methylaminothiocarbonyl-4-methoxyphenyl-N-2-pentylacetamide
(44) 3-Sulfonylamino-N-methylaminothiocarbonyl-4-methoxyphenyl-N-3-pentylacetamide
(45) 3-Sulfonylamino-N-methylaminothiocarbonyl-4-methoxyphenyl-N-1-butyl-2-methylacetamide
(46) 3-Sulfonylamino-N-methylaminothiocarbonyl-4-methoxyphenyl-N-1-butyl-3-methylacetamide
(47) 3-Sulfonylamino-N-methylaminothiocarbonyl-4-methoxyphenyl-N-1-hexylacetamide
(48) 3-Sulfonylamino-N-methylaminothiocarbonyl-4-methoxyphenyl-N-2-hexylacetamide
(49) 3-Sulfonylamino-N-methylaminothiocarbonyl-4-methoxyphenyl-N-3-hexylacetamide
(50) 3-Sulfonylamino-N-methylaminothiocarbonyl-4-methoxyphenyl-N-1-heptylacetamide
(51) 3-Sulfonylamino-N-methylaminothiocarbonyl-4-methoxyphenyl-N-2-heptylacetamide
(52) 3-Sulfonylamino-N-methylaminothiocarbonyl-4-methoxyphenyl-N-3-heptylacetamide
(53) 3-Sulfonylamino-N-methylaminothiocarbonyl-4-methoxyphenyl-N-1-octylacetamide
(54) 3-Sulfonylamino-N-methylaminothiocarbonyl-4-methoxyphenyl-N-2-octylacetamide
(55) 3-Sulfonylamino-N-methylaminothiocarbonyl-4-methoxyphenyl-N-1-adamantylacetamide
(56) 3-Sulfonylamino-N-methylaminothiocarbonyl-4-methoxyphenyl-N-2-adamantylacetamide
(57) 3-Sulfonylamino-N-methylaminothiocarbonyl-4-methoxyphenyl-N-dimethylacetamide
(58) 3-Sulfonylamino-N-methylaminothiocarbonyl-4-methoxyphenyl-N-methyl-N'-ethylacetamide
(59) 3-Sulfonylamino-N-methylaminothiocarbonyl-4-methoxyphenyl-N-methyl-N'-1-propylacetamide
(60) 3-Sulfonylamino-N-methylaminothiocarbonyl-4-methoxyphenyl-N-methyl-N'-2-propylacetamide
(61) 3-Sulfanylamino-N-methylaminothiocarbonyl-4-methoxyphenyl-N-methyl-N'-1-butylacetamide
(62) 3-Sulfonylamino-N-methylaminothiocarbonyl-4-methoxyphenyl-N-methyl-N'-2-butylacetamide
(63) 3-Sulfonylamino-N-methylaminothiocarbonyl-4-methoxyphenyl-N-diethylacetamide
(64) 3-Sulfonylamino-N-methylaminothiocarbonyl-4-methoxyphenyl-N-ethyl-N'-1-propylacetamide
(65) 3-Sulfonylamino-N-methylaminothiocarbonyl-4-methoxyphenyl-N-ethyl-N'-2-propylacetamide
(66) 3-Sulfonylamino-N-methylaminothiocarbonyl-4-methoxyphenylpyrrolidinylacetamide
(67) 3-Sulfonylamino-N-methylaminothiocarbonyl-4-methoxyphenylpiperidylacetamide
(68) 3-Sulfonylamino-N-methylaminothiocarbonyl-4-methoxyphenylmorpholinoacetamide
(69) 3-Sulfonylamino-N-methylaminothiocarbonyl-4-methoxyphenyl-N-methylpiperazinylacetamide
(70) 3-Sulfonylamino-N-methylaminothiocarbonyl-4-methoxyphenyl-4-thiomorpholinylacetamide
(71) 3-Sulfonylamino-N-methylaminocarbonyl-4-methoxyphenyl-N-methylpropionamide
(72) 3-Sulfonylamino-N-methylaminocarbonyl-4-methoxyphenyl-N-ethylpropionamide
(73) 3-Sulfonylamino-N-methylaminocarbonyl-4-methoxyphenyl-N-1-propylpropionamide
(74) 3-Sulfonylamino-N-methylaminocarbonyl-4-methoxyphenyl-N-2-propylpropionamide
(75) 3-Sulfonylamino-N-methylaminocarbonyl-4-methoxyphenyl-N-1-butylpropionamide
(76) 3-Sulfonylamino-N-methylaminocarbonyl-4-methoxyphenyl-N-2-butylpropionamide
(77) 3-Sulfonylamino-N-methylaminocarbonyl-4-methoxyphenyl-N-1-pentylpropionamide
(78) 3-Sulfonylamino-N-methylaminocarbonyl-4-methoxyphenyl-N-2-pentylpropionamide
(79) 3-Sulfonylamino-N-methylaminocarbonyl-4-methoxyphenyl-N-3-pentylpropionamide
(80) 3-Sulfonylamino-N-methylaminocarbonyl-4-methoxyphenyl-N-1-butyl-2-methylpropionamide
(81) 3-Sulfonylamino-N-methylaminocarbonyl-4-methoxyphenyl-N-1-butyl-3-methylpropionamide
(82) 3-Sulfonylamino-N-methylaminocarbonyl-4-methoxyphenyl-N-1-hexylpropionamide
(83) 3-Sulfonylamino-N-methylaminocarbonyl-4-methoxyphenyl-N-2-hexylpropionamide
(84) 3-Sulfonylamino-N-methylaminocarbonyl-4-methoxyphenyl-N-3-hexylpropionamide
(85) 3-Sulfonylamino-N-methylaminocarbonyl-4-methoxyphenyl-N-1-heptylpropionamide
(86) 3-Sulfonylamino-N-methylaminocarbonyl-4-methoxyphenyl-N-2-heptylpropionamide
(87) 3-Sulfonylamino-N-methylaminocarbonyl-4-methoxyphenyl-N-3-heptylpropionamide
(88) 3-Sulfonylamino-N-methylaminocarbonyl-4-methoxyphenyl-N-1-octylpropionamide
(89) 3-Sulfonylamino-N-methylaminocarbonyl-4-methoxyphenyl-N-2-octylpropionamide
(90) 3-Sulfonylamino-N-methylaminocarbonyl-4-methoxyphenyl-N-1-adamantylpropionamide
(91) 3-Sulfonylamino-N-methylaminocarbonyl-4-methoxyphenyl-N-2-adamantylpropionamide
(92) 3-Sulfonylamino-N-methylaminocarbonyl-4-methoxyphenyl-N-dimethylpropionamide
(93) 3-Sulfonylamino-N-methylaminocarbonyl-4-methoxyphenyl-N-methyl-N'-ethylpropionamide

(94) 3-Sulfonylamino-N-methylaminocarbonyl-4-methoxyphenyl-N-methyl-N'-1-propylpropionamide
(95) 3-Sulfonylamino-N-methylaminocarbonyl-4-methoxyphenyl-N-methyl-N'-2-propylpropionamide
(96) 3-Sulfonylamino-N-methylaminocarbonyl-4-methoxyphenyl-N-methyl-N'-1-butylpropionamide
(97) 3-Sulfonylamino-N-methylaminocarbonyl-4-methoxyphenyl-N-methyl-N'-2-butylpropionamide
(98) 3-Sulfonylamino-N-methylaminocarbonyl-4-methoxyphenyl-N-diethylpropionamide
(99) 3-Sulfonylamino-N-methylaminocarbonyl-4-methoxyphenyl-N-ethyl-N'-1-propylpropionamide
(100) 3-Sulfonylamino-N-methylaminocarbonyl-4-methoxyphenyl-N-ethyl-N'-2-propylpropionamide
(101) 3-Sulfonylamino-N-methylaminocarbonyl-4-methoxyphenylpyrrolidinylpropionamide
(102) 3-Sulfonylamino-N-methylaminocarbonyl-4-methoxyphenylpiperidylpropionamide
(103) 3-Sulfonylamino-N-methylaminocarbonyl-4-methoxyphenylmorpholinopropionamide
(104) 3-Sulfonylamino-N-methylaminocarbonyl-4-methoxyphenyl-N-methylpiperazinylpropionamide
(105) 3-Sulfonylamino-N-methylaminocarbonyl-4-methoxyphenyl-4-thiomorpholinylpropionamide
(106) 3-Sulfonylamino-N-methylaminothiocarbonyl-4-methoxy-phenyl-N-methylpropionamide
(107) 3-Sulfonylamino-N-methylaminothiocarbonyl-4-methoxy-phenyl-N-ethylpropionamide
(108) 3-Sulfonylamino-N-methylaminothiocarbonyl-4-methoxy-phenyl-N-1-propylpropionamide
(109) 3-Sulfonylamino-N-methylaminothiocarbonyl-4-methoxy-phenyl-N-2-propylpropionamide
(110) 3-Sulfonylamino-N-methylaminothiocarbonyl-4-methoxy-phenyl-N-1-butylpropionamide
(111) 3-Sulfonylamino-N-methylaminothiocarbonyl-4-methoxy-phenyl-N-2-butylpropionamide
(112) 3-Sulfonylamino-N-methylaminothiocarbonyl-4-methoxy-phenyl-N-1-pentylpropionamide
(113) 3-Sulfonylamino-N-methylaminothiocarbonyl-4-methoxy-phenyl-N-2-pentylpropionaimide
(114) 3-Sulfonylamino-N-methylaminothiocarbonyl-4-methoxy-phenyl-N-3-pentylpropionamide
(115) 3-Sulfonylamino-N-methylaminothiocarbonyl-4-methoxy-phenyl-N-1-butyl-2-methylpropionamide
(116) 3-Sulfonylamino-N-methylaminothiocarbonyl-4-methoxy-phenyl-N-1-butyl-3-methylpropionamide
(117) 3-Sulfonylamino-N-methylaminothiocarbonyl-4-methoxy-phenyl-N-1-hexylpropionamide
(118) 3-Sulfonylamino-N-methylaminothiocarbonyl-4-methoxy-phenyl-N-2-hexylpropionamide
(119) 3-Sulfonylamino-N-methylaminothiocarbonyl-4-methoxy-phenyl-N-3-hexylpropionamide
(120) 3-Sulfonylamino-N-methylaminothiocarbonyl-4-methoxy-phenyl-N-1-heptylpropionamide
(121) 3-Sulfonylamino-N-methylaminothiocarbonyl-4-methoxy-phenyl-N-2-heptylpropionamide
(122) 3-Sulfonylamino-N-methylaminothiocarbonyl-4-methoxy-phenyl-N-3-heptylpropionamide
(123) 3-Sulfonylamino-N-methylaminothiocarbonyl-4-methoxy-phenyl-N-1-octylpropionamide
(124) 3-Sulfonylamino-N-methylaminothiocarbonyl-4-methoxy-phenyl-N-2-octylpropionamide
(125) 3-Sulfonylamino-N-methylaminothiocarbonyl-4-methoxy-phenyl-N-1-adamantylpropionamide
(126) 3-Sulfonylamino-N-methylaminothiocarbonyl-4-methoxy-phenyl-N-2-adamantylpropionamide
(127) 3-Sulfonylamino-N-methylaminothiocarbonyl-4-methoxy-phenyl-N-dimethylpropionamide
(128) 3-Sulfonylamino-N-methylaminothiocarbonyl-4-methoxy-phenyl-N-methyl-N'-ethylpropionamide
(129) 3-Sulfonylamino-N-methylaminothiocarbonyl-4-methoxy-phenyl-N-methyl-N'-1-propylpropionamide
(130) 3-Sulfonylamino-N-methylaminothiocarbonyl-4-methoxy-phenyl-N-methyl-N'-2-propylpropionamide
(131) 3-Sulfonylamino-N-methylaminothiocarbonyl-4-methoxy-phenyl-N-methyl-N'-1-butylpropionamide
(132) 3-Sulfonylamino-N-methylaminothiocarbonyl-4-methoxy-phenyl-N-methyl-N'-2-butylpropionamide
(133) 3-Sulfonylamino-N-methylaminothiocarbonyl-4-methoxy-phenyl-N-diethylpropionamide
(134) 3-Sulfonylamino-N-methylaminothiocarbonyl-4-methoxy-phenyl-N-ethyl-N'-1-propylpropionamide
(135) 3-Sulfonylamino-N-methylaminothiocarbonyl-4-methoxy-phenyl-N-ethyl-N'-2-propylpropionamide
(136) 3-Sulfonylamino-N-methylaminothiocarbonyl-4-methoxy-phenylpyrrolidinylpropionamide
(137) 3-Sulfonylamino-N-methylaminothiocarbonyl-4-methoxy-phenylpiperidylpropionamide
(138) 3-Sulfonylamino-N-methylaminothiocarbonyl-4-methoxy-phenylmorpholinopropionamide
(139) 3-Sulfonylamino-N-methylaminothiocarbonyl-4-methoxy-phenyl-N-methylpiperazinylpropionamide
(140) 3-Sulfonylamino-N-methylaminothiocarbonyl-4-methoxy-phenyl-4-thiomorpholinylpropionamide
(141) 3-Sulfonylamino-N-methylaminothiocarbonyl-4-methylphenyl-N-methylacetamide
(142) 3-Sulfonylamino-N-methylaminothiocarbonyl-4-methylphenyl-N-ethylacetamide
(143) 3-Sulfonylamino-N-methylaminothiocarbonyl-4-methylphenyl-N-1-propylacetamide
(144) 3-Sulfonylamino-N-methylaminothiocarbonyl-4-methylphenyl-N-2-propylacetamide
(145) 3-Sulfonylamino-N-methylaminothiocarbonyl-4-methylphenyl-N-1-butylacetamide
(146) 3-Sulfonylamino-N-methylaminothiocarbonyl-4-methylphenyl-N-2-butylacetamide
(147) 3-Sulfonylamino-N-methylaminothiocarbonyl-4-methylphenyl-N-1-pentylacetamide
(148) 3-Sulfonylamino-N-methylaminothiocarbonyl-4-methylphenyl-N-2-pentylacetamide
(149) 3-Sulfonylamino-N-methylaminothiocarbonyl-4-methylphenyl-N-3-pentylacetamide
(150) 3-Sulfonylamino-N-methylaminothiocarbonyl-4-methylphenyl-N-1-butyl-2-methylacetamide
(151) 3-Sulfonylamino-N-methylaminothiocarbonyl-4-methylphenyl-N-1-butyl-3-methylacetamide
(152) 3-Sulfonylamino-N-methylaminothiocarbonyl-4-methylphenyl-N-1-hexylacetamide
(153) 3-Sulfonylamino-N-methylaminothiocarbonyl-4-methylphenyl-N-2-hexylacetamide
(154) 3-Sulfonylamino-N-methylaminothiocarbonyl-4-methylphenyl-N-3-hexylacetamide
(155) 3-Sulfonylamino-N-methylaminothiocarbonyl-4-methylphenyl-N-1-heptylacetamide
(156) 3-Sulfonylamino-N-methylaminothiocarbonyl-4-methylphenyl-N-2-heptylacetamide
(157) 3-Sulfonylamino-N-methylaminothiocarbonyl-4-methylphenyl-N-3-heptylacetamide
(158) 3-Sulfonylamino-N-methylaminothiocarbonyl-4-methylphenyl-N-1-octylacetamide
(159) 3-Sulfonylamino-N-methylaminothiocarbonyl-4-methylphenyl-N-2-octylacetamide
(160) 3-Sulfonylamino-N-methylaminothiocarbonyl-4-methylphenyl-N-1-adamantylacetamide
(161) 3-Sulfonylamino-N-methylaminothiocarbonyl-4-methylphenyl-N-2-adamantylacetamide (162) 3-Sulfonylamino-N-methylaminothiocarbonyl-4-methylphenyl-N-dimethylacetamide
(163) 3-Sulfonylamino-N-methylaminothiocarbonyl-4-methylphenyl-N-methyl-N'-ethylacetamide
(164) 3-Sulfonylamino-N-methylaminothiocarbonyl-4-methylphenyl-N-methyl-N'-1-propylacetamide
(165) 3-Sulfonylamino-N-methylaminothiocarbonyl-4-methylphenyl-N-methyl-N'-2-propylacetamide
(166) 3-Sulfonylamino-N-methylaminothiocarbonyl-4-methphenyl-N-methyl-N'-1-butylacetamide
(167) 3-Sulfonylamino-N-methylaminothiocarbonyl-4-methylphenyl-N-methyl-N'-2-butylacetamide
(168) 3-Sulfonylamino-N-methylaminothiocarbonyl-4-methylphenyl-N-diethylacetamide
(169) 3-Sulfonylamino-N-methylaminothiocarbonyl-4-methylphenyl-N-ethyl-N'-1-propylacetamide
(170) 3-Sulfonylamino-N-methylaminothiocarbonyl-4-methylphenyl-N-ethyl-N'-2-propylacetamide
(171) 3-Sulfonylamino-N-methylaminothiocarbonyl-4-methylphenylpyrrolidinylacetamide
(172) 3-Sulfonylamino-N-methylaminothiocarbonyl-4-methylphenylpiperidylacetamide
(173) 3-Sulfonylamino-N-methylaminothiocarbonyl-4-methylphenylmorpholinoacetamide
(174) 3-Sulfonylamino-N-methylaminothiocarbonyl-4-methylphenyl-N-methylpiperazinylacetamide
(175) 3-Sulfonylamino-N-methylaminothiocarbonyl-4-methylphenyl-4-thiomorpholinylacetamide
(176) 3-Sulfonylamino-N-methylaminothiocarbonyl-4-methylphenyl-N-methylpropionamide
(177) 3-Sulfonylamino-N-methylaminothiocarbonyl-4-methylphenyl-N-methylpropionamide
(178) 3-Sulfonylamino-N-methylaminothiocarbonyl-4-methylphenyl-N-1-propylpropionamide
(179) 3-Sulfonylamino-N-methylaminothiocarbonyl-4-methylphenyl-N-2-propylpropionamide
(180) 3-Sulfonylamino-N-methylaminothiocarbonyl-4-methylphenyl-N-1-butylpropionamide
(181) 3-Sulfonylamino-N-methylaminothiocarbonyl-4-methylphenyl-N-2-butylpropionamide
(182) 3-Sulfonylamino-N-methylaminothiocarbonyl-4-methylphenyl-N-1-pentylpropionamide
(183) 3-Sulfonylamino-N-methylaminothiocarbonyl-4-methylphenyl-N-2-pentylpropionamide
(184) 3-Sulfonylamino-N-methylaminothiocarbonyl-4-methylphenyl-N-3-pentylpropionamide
(185) 3-Sulfonylamino-N-methylaminothiocarbonyl-4-methylphenyl-N-1-butyl-2-methylpropionamide
(186) 3-Sulfonylamino-N-methylaminothiocarbonyl-4-methylphenyl-N-1-butyl-3-methylpropionamide
(187) 3-Sulfonylamino-N-methylaminothiocarbonyl-4-methphenyl-N-1-hexylpropionamide
(188) 3-Sulfonylamino-N-methylaminothiocarbonyl-4-methylphenyl-N-2-hexylpropionamide
(189) 3-Sulfonylamino-N-methylaminothiocarbonyl-4-methylphenyl-N-3-hexylpropionamide
(190) 3-Sulfonylamino-N-methylaminothiocarbonyl-4-methphenyl-N-1-heptylpropionamide
(191) 3-Sulfonylamino-N-methylaminothiocarbonyl-4-methylphenyl-N-2-heptylpropionamide
(192) 3-Sulfonylamino-N-methylaminothiocarbonyl-4-methylphenyl-N-3-heptylpropionamide
(193) 3-Sulfonylamino-N-methylaminothiocarbonyl-4-methylphenyl-N-1-octylpropionamide
(194) 3-Sulfonylamino-N-methylaminothiocarbonyl-4-methylphenyl-N-2-octylpropionamide
(195) 3-Sulfonylamino-N-methylaminothiocarbonyl-4-methylphenyl-N-1-adamantylpropionamide
(196) 3-Sulfonylamino-N-methylaminothiocarbonyl-4-methylphenyl-N-2-adamantylpropionamide
(197) 3-Sulfonylamino-N-methylaminothiocarbonyl-4-methylphenyl-N-dimethylpropionamide
(198) 3-Sulfonylamino-N-methylaminothiocarbonyl-4-methylphenyl-N-methyl-N'-ethylpropionamide
(199) 3-Sulfonylamino-N-methylaminothiocarbonyl-4-methylphenyl-N-methyl-N'-1-propylpropionamide
(200) 3-Sulfonylamino-N-methylaminothiocarbonyl-4-methylphenyl-N-methyl-N'-2-propylpropionamide
(201) 3-Sulfonylamino-N-methylaminothiocarbonyl-4-methylphenyl-N-methyl-N'-1-butylpropionamide
(202) 3-Sulfonylamino-N-methylaminothiocarbonyl-4-methylphenyl-N-methyl-N'-2-butylpropionamide
(203) 3-Sulfonylamino-N-methylaminothiocarbonyl-4-methylphenyl-N-diethylpropionamide
(204) 3-Sulfonylamino-N-methylaminothiocarbonyl-4-methylphenyl-N-ethyl-N'-1-propylpropionamide
(205) 3-Sulfonylamino-N-methylaminothiocarbonyl-4-methylphenyl-N-ethyl-N'-2-propylpropionamide
(206) 3-Sulfonylamino-N-methylaminothiocarbonyl-4-methylphenylpyrrolidinylpropionamide
(207) 3-Sulfonylamino-N-methylaminothiocarbonyl-4-methylphenylpiperidylpropionamide
(208) 3-Sulfonylamino-N-methylaminothiocarbonyl-4-methylphenylmorpholinopropionamide
(209) 3-Sulfonylamino-N-methylaminothiocarbonyl-4-methylphenyl-N-methylpiperazinylpropionamide
(210) 3-Sulfonylamino-N-methylaminothiocarbonyl-4-methylphenyl-4-thiomorpholinylpropionamide Preparation of the Starting Materials Preparation of 3-Sulfonylaminophenylcarboxylic Acids The 4-substituted phenylcarboxylic acids were added in portions with stirring to an excess of chlorosulfonic acid. The mixture was stirred for 30 minutes at room temperature, then poured onto ice and the resulting sulfonyl chloride was filtered off with suction. The latter was dissolved in ammonia solution, stirred at room temperature for 30 minutes, and the solution was neutralized using 2N hydrochloric acid. The product obtained was filtered off with suction. Prepared according to this method:

3-Sulfonylamino-4-methoxyphenyl-3-propionic acid
M.p. 172–1760° C.

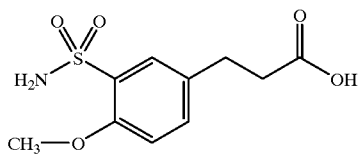

3-Sulfonylamino-4-methoxyphenylacetic acid
M.p. 1640° C.

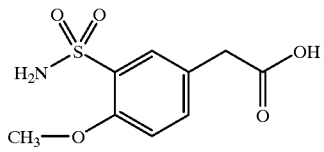

3-Sulfonylamino-4-ethoxyphenylacetic acid
M.p. 183–185° C.

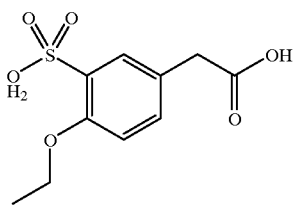

Preparation of 3-sulfonylamino-N-methylaminothiocarbonyl-4-methoxyphenylacetic acid

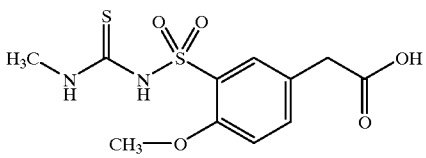

5 g of 3-sulfonylamino-4-methoxyphenylacetic acid were dissolved in 3 ml of DMF and stirred at 40° C. for 30 minutes with 245 mg of sodium hydroxide. 328 mg of methyl isothiocyanate were added thereto and the mixture was stirred for a further 2 h at 70° C. 2N hydrochloric acid was added to the cooled solution and the product was filtered off with suction. M.p. 1740° C.

The following was prepared by an analogous procedure:
3-Sulfonylamino-N-methylaminothiocarbonyl-4-ethoxyphenyl-acetic acid
M.p. 152–154° C.

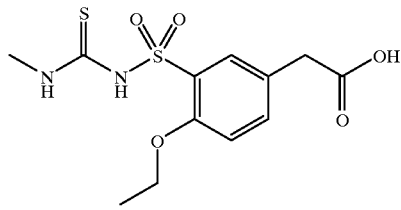

EXAMPLES

Example 1

3-Sulfonylamino-N-methylaminothiocarbonyl-4-methoxyphenyl-N-cyclohexylpropionamide

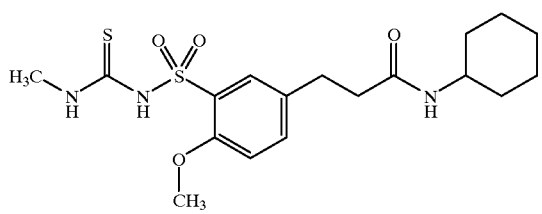

500 mg of 3-sulfonylamino-4-methoxyphenyl-N-cyclohexypropionamide were dissolved in 10 ml of DMF, treated with 88 mg of NaOH and stirred at 400° C. for 30 min. 107 mg of methyl isothiocyanate were then added and the mixture was stirred at 70° C. for a further 2 h. After cooling and neutralizing with 2N hydrochloric acid, the product was filtered off with suction and dried.
M.p. 163° C.

Example 2

3-Sulfonylamnno-N-methylrninothiocarbonyl-4-methoxyphenyl-N-cyclohexylacetamide

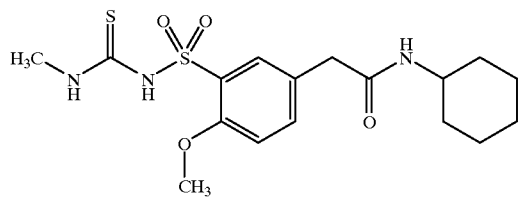

Analogously, 360 mg of 3-sulfonylamino-N-methylaminothiocarbonyl-4-methoxyphenyl-N-cyclohexylacetamide were prepared from 500 mg of 3-sulfonylamino-4-methoxyphenyl-N-cyclohexylacetamide.
M.p. 185° C.

Example 3

3-Sulfonylamino-N-methylaminothiocarbonyl-4-methoxyphenyl-N-3-pentylacetamide

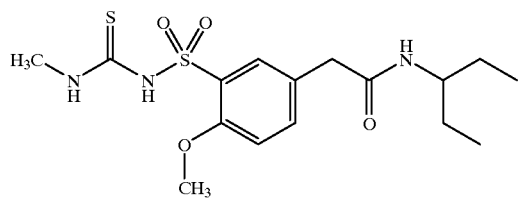

400 mg of 3-sulfonylamino-N-methylaminothiocarbonyl-4-methoxyphenylacetic acid were dissolved in 5 ml of THF and treated with 224 mg of carbonyldiimidazole. The mixture was stirred at room temperature for 2 h. After the addition of 120 mg of 3-aminopentane, it was stirred overnight at room temperature. The amount of solvent was reduced in vacuo and the residue was added to 2N HCl. The solid was filtered off with suction.
M.p. 169° C.

Example 4

3-Sulfonylamino-N-methylalminothiocarbonyl-4-methoxyphenyl-N-(R)-1-cyclohexyl-1-ethylacetamide

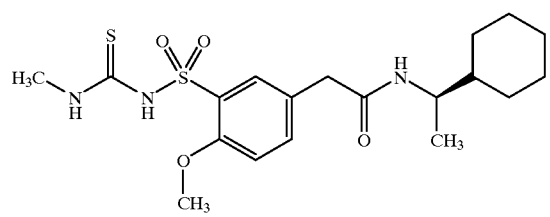

Analogously to Example 3, 3-sulfonylamino-N-methylaminothiocarbonyl-4-methoxyphenyl-N-(R)-1- cyclohexyl-1-ethylacetamide was obtained from 300 mg of 3-sulfonylamino-N-methylaminothiocarbonyl-4-methoxyphenylacetic acid and 144 mg of (R)-1-cyclohexyl-1-ethylamine. M.p. 84° C.

Example 5

3-Sulfonylamino-N-methylaminothiocarbonyl-4-methoxyphenyl-N-(S)-1-cyclohexyl-1-ethylacetamide

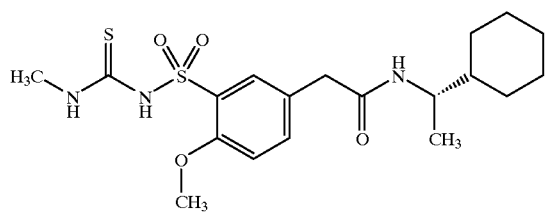

Analogously to Example 3, 3-sulfonylamino-N-methylaminothiocarbonyl-4-methoxyphenyl-N-(S)-1-cyclohexyl-1-ethylacetaimide was obtained from 300 mg of 3-sulfonylamino-N-methylaminothiocarbonyl-4-methoxyphenylacetic acid and 144 mg of (S)-1-cyclohexyl-1-ethylamine.

M.p. 84° C.

Example 6

3-Sulfonylamino-N-methylaminothiocarbonyl-4-methoxyphenyl-N-1-butylacetamide

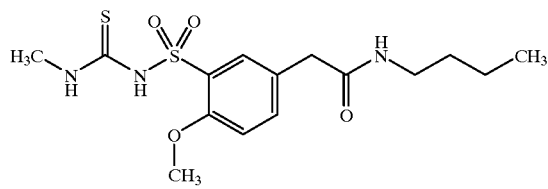

Analogously to Example 3, the product was obtained from 300 mg of 3-sulfonylamino-N-methylaminothiocarbonyl-4-methoxyphenylacetic acid and 83 mg of butylamine.

M.p. 136° C.

Example 7

3-Sulfonylamino-N-methylaminothiocarbonyl-4-methoxyphenyl-N-isopropylpropionamide

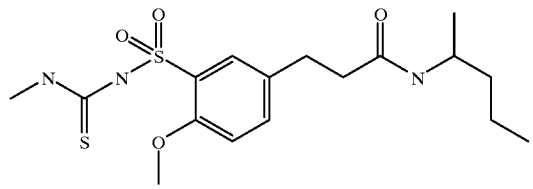

M.p.: 116° C.

Example 8

3-Sulfonylamino-N-methylaminothiocarbonyl-4-methoxyphenyl-N-isopropylpropionamide

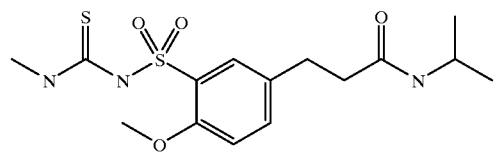

M.p.: 172° C.

Example 9

3-Sulfonylamino-N-methylaminothiocarbonyl-4-methoxyphenyl-N-2-pentylacetamide

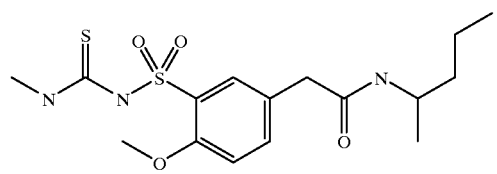

M.p.: 137° C.

Example 10

3-Sulfonylamino-N-methylaminothiocarbonyl-4-methoxyphenyl-N-isopropylacetamide

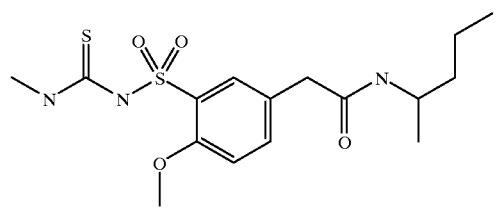

Oil.

Example 11

3-Sulfonylamino-N-methylaminothiocarbonyl-4-methoxyphenyl-N-2-(R)-butylacetamide

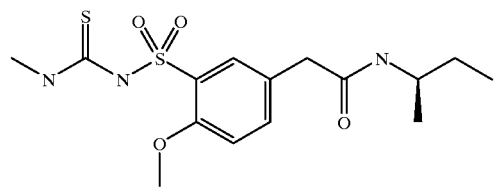

M.p.: 123° C.

Example 12

3-Sulfonylamino-N-methylaminothiocarbonyl-4-methoxyphenyl-N-2-(S)-butylacetamide

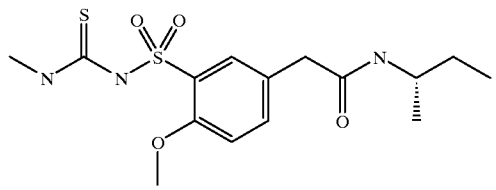

M.p.: 119° C.

Example 13

3-Sulfonylamino-N-methylaminothiocarbonyl-4-methoxyphenyl-N-4-heptylacetamide

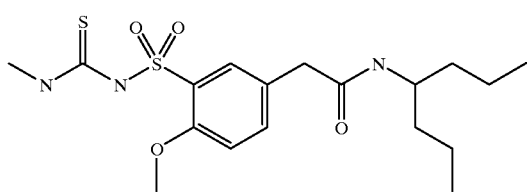

M.p.: 118° C.

Example 14

3-Sulfonylamino-N-methylaminothiocarbonyl-4-methoxyphenyl-N-6-methyl-2-heptylacetamide

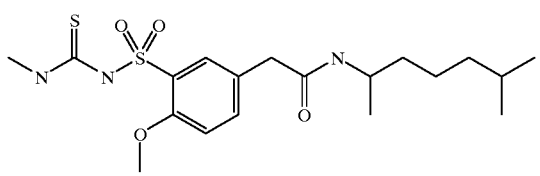

M.p.: 113° C.

Example 15

3-Sulfonylamino-N-methylaminothiocarbonyl-4-methoxyphenyl-N-2-undecylacetamide

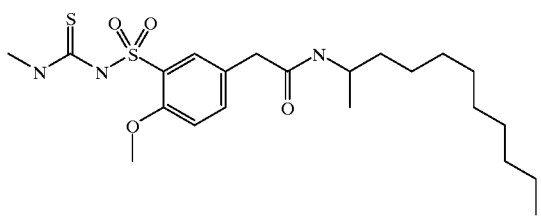

Oil.

Example 16

3-Sulfonylamino-N-methylaminothiocarbonyl-4-methoxyphenyl-N-2-hexylacetamide

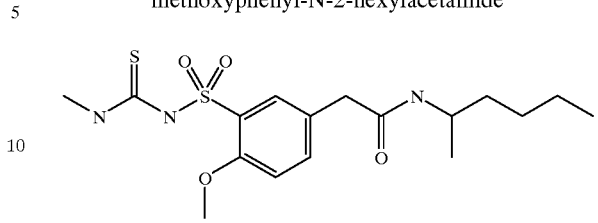

M.p.:111° C.

Example 17

3-Sulfonylamino-N-methylaminocarbonyl-4-methoxyphenyl-N-3, 3-dimethyl-2-butylacetamide

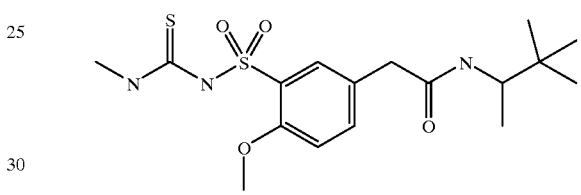

M.p.: 170° C.

Example 18

3-Sulfonylamino-N-methylaminothiocarbonyl-4-methoxyphenyl-N-2-(S)-heptylacetamide

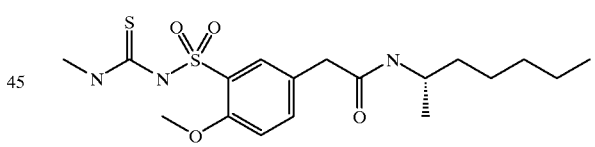

M.p.: 139° C.

Example 19

3-Sulfonylamino-N-methylaminothiocarbonyl-4-methoxyphenyl-N-2-(R)-heptylacetamide

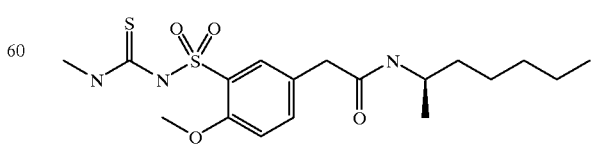

M.p.: 138° C.

Example 20

3-Sulfonylamino-N-methylaminothiocarbonyl-4-methoxyphenyl-N-2-octylacetamide

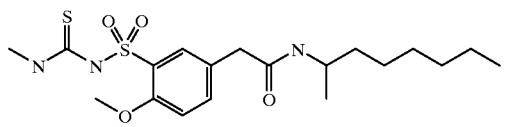

M.p.: 103° C.

Example 21

3-Sulfonylamino-N-methylaminothiocarbonyl-4-methoxyphenyl-N-6-2-methylheptan-2-ole-acetamide

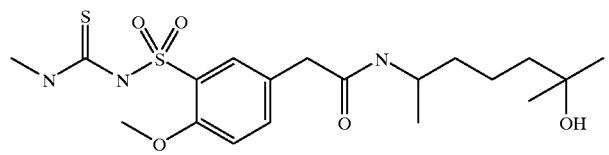

M.p.: 85° C.

Example 22

3-Sulfonylamino-N-methylaminothiocarbonyl-4-methoxyphenyl-N-2-(S)-pentylacetamide

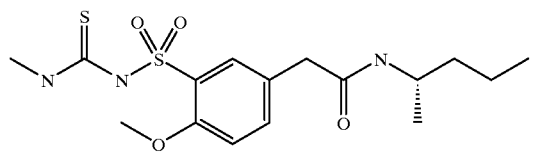

M.p.: 102° C.

Example 23

3-Sulfonylamino-N-methylaminothiocarbonyl-4-ethoxyphenyl-N-4-heptylacetamide

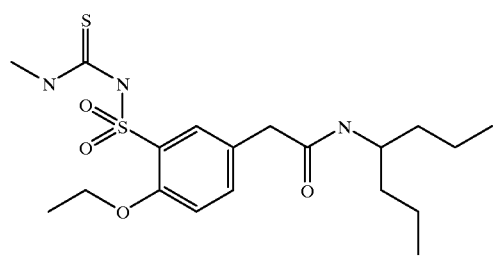

M.p.: 157° C.

Example 24

3-Sulfonylamino-N-methylaminothiocarbonyl-4-ethoxyphenyl-N-(S)-1-cyclohexylethylacetamide

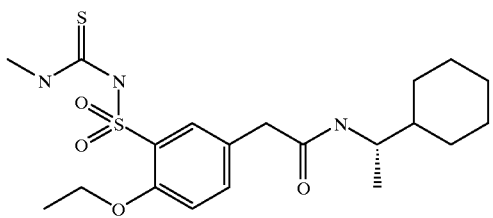

M.p.: 162° C.

Example 25

3-Sulfonylamino-N-methylaminothiocarbonyl-4-ethoxyphenyl-N-6-methyl2-heptylacetamide

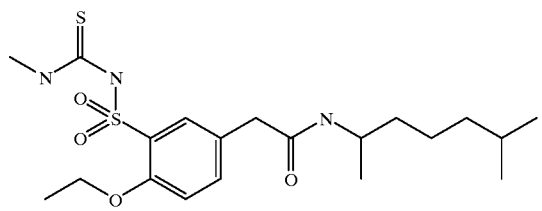

M.p.: 122° C.

Example 26

3-Sulfonylamino-N-methylaminothiocarbonyl-4-ethoxyphenyl-N-2-(S)-heptylacetamide

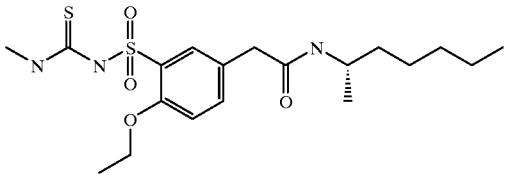

M.p.: 137° C.

Example 27

3-Sulfonylamino-N-methylaminocarbonyl-4-ethoxyphenyl-N-2-(S)-heptylacetamide

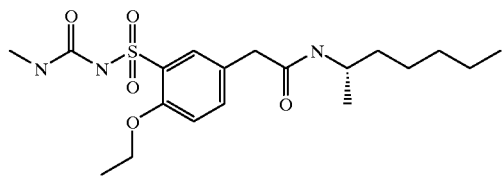

M.p.: 151° C.

Example 28

3-Sulfonylamino-N-methylaminothiocarbonyl-4-ethoxyphenyl-N-2-octylacetamide

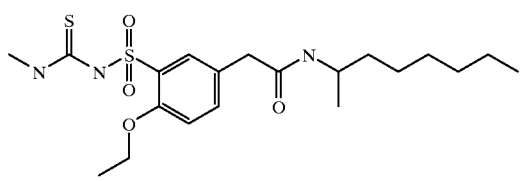

M.p.: 123° C.

Example 29

3-Sulfonylamino-N-methylaminothiocarbonyl-4-ethoxyphenyl-N-1-adamantylacetamide

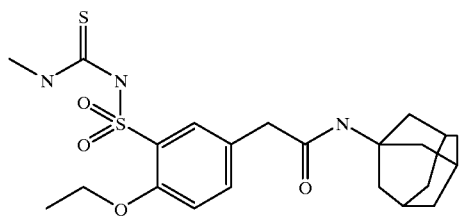

M.p.: 170° C.

Example 30

3-Sulfonylamino-N-methylaminothiocarbonyl-4-methoxyplenyl-N-n-heptylacetamide

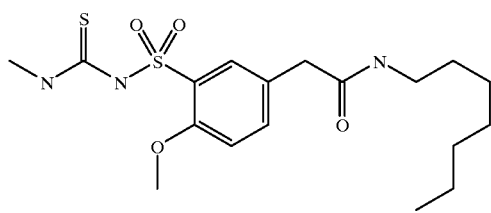

M.p.: 139° C.

Example 31

3-Sulfonylamino-N-methylaminothiocarbonyl-4-methoxyphenyl-N-n-octylacetamide

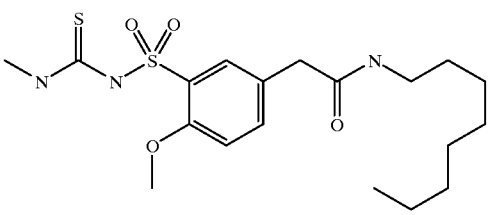

M.p.: 132° C.

Example 32

3-Sulfonylamino-N-methylaminothiocarbonyl-4-methoxyphenyl-N-n-nonylarcetamide

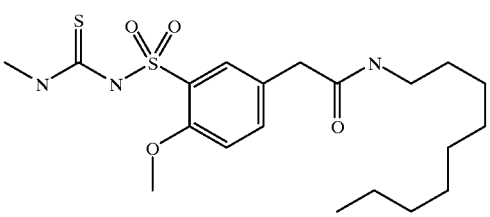

M.p.: 134° C.

Example 33

3-Sulfonylamino-N-methylaminocarbonyl-4-methoxyphenyl-N-2-(S)-heptylacetamide

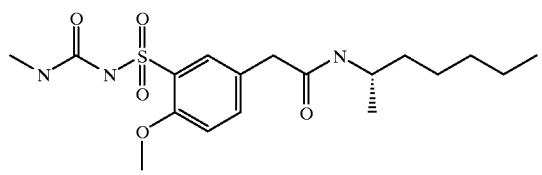

M.p.: 178° C.

Example 34

3-Sulfonylamino-N-methylaminocarbonyl-4-methoxyphenyl-N-2-octylacetamide

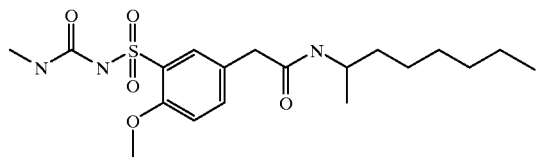

Oil

Example 35

1-[3-Sulfonylamino-N-methylaminothiocarbonyl-4-methoxyphenyl]-1-cyclopropane-N-2-(S)-heptylcyclopropane-1-carboxamide

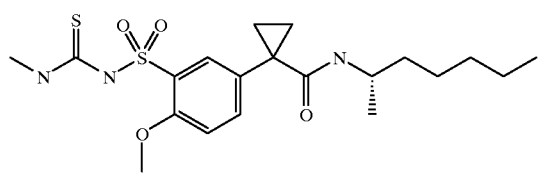

M.p.: 184° C.

Example 36

3-Sulfonylamino-N-ethylaminothiocarbonyl-4-methoxyphenyl-N-2-octylacetamide

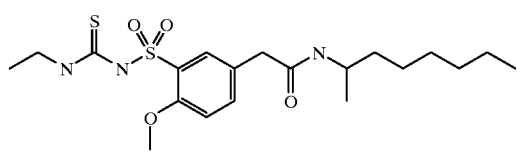

M.p.: 125° C.

Example 37

3-Sulfonylamino-N-isopropylaminothiocarbonyl-4-methoxyphenyl-N-2-octylacetamide

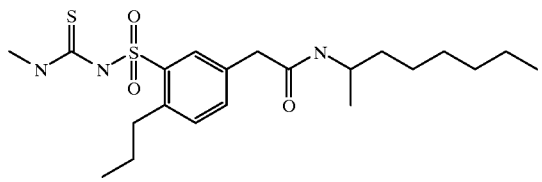

M.p.: 141° C.

Example 38

3-Sulfonylamino-N-cyclopropylaminothiocarbonyl-4-methoxyphenyl-N-2-octylacetamide

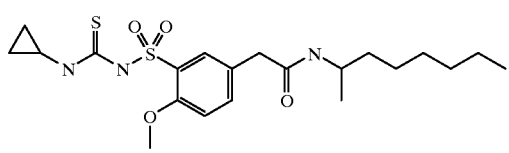

M.p.: 128° C.

Example 39

3-Sulfonylamino-N-cyclohexylaminothiocarbonyl-4-methoxyphenyl-N-2-octylacetamide

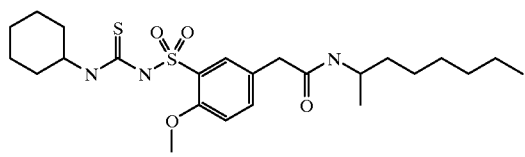

Oil.

Example 40

3-Sulfonylamino-N-isopropylaminocarbonyl-4-methoxyphenyl-N-2-octylacetamide

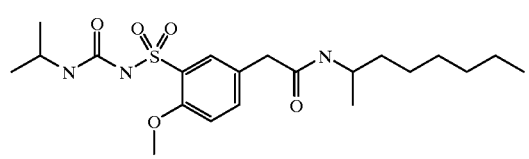

M.p.: 118° C.

Example 41

3-Sulfonylamino-N-cyclopropylaminocarbonyl-4-methoxyphenyl-N-2-octylacetamide

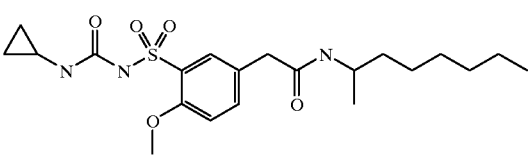

Oil.

Example 42

3-Sulfonylamino-N-ethylaminocarbonyl-4-methoxyphenyl-N-2-octylacetamide

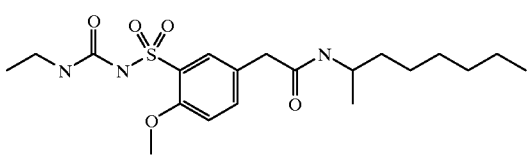

Oil.

Example 43

3-Sulfonylamino-N-methylaminocarbonyl-4-ethoxyphenyl-N-2-octylacetamide

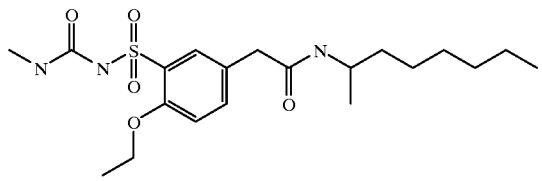

M.p.: 78° C.

Example 44

3-Sulfonylamino-N-isopropylaminothiocarbonyl-4-methoxyphenyl-N-2-octylacetamide

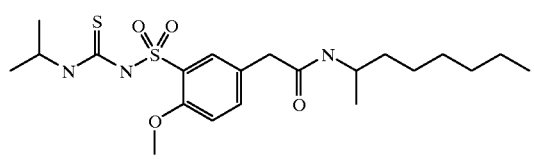

M.p.: 141° C.

Example 45

3-Sulfonylamino-N-methylaminothiocarbonyl-4-methoxyphenyl-N-4-nonylacetamide

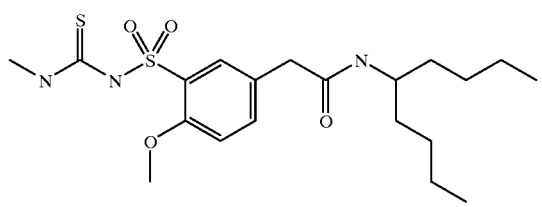

M.p.: 145° C.

Example 46

3-Sulfonylamino-N-methylaminothiocarbonyl-4-methoxyphenyl-N-3-heptylacetamide

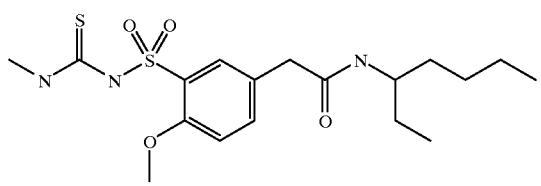

M.p.: 100° C.

Example 47

3-Sulfonylamino-N-methylaminocarbonyl-4-methoxyphenyl-N-2-nonylacetamide

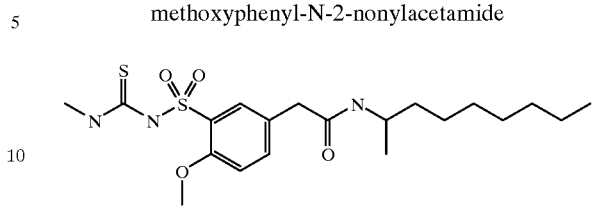

M.p.: 107° C.

Example 48

3-Sulfonylamino-N-ethylaminothiocarbonyl-4-methoxyphenyl-N-2-(S)-heptylacetamide

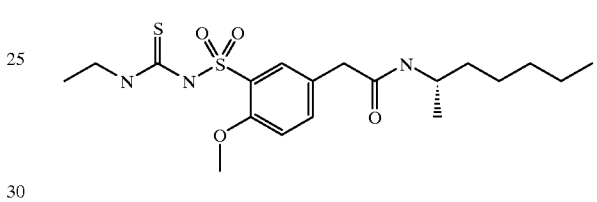

M.p.: 145° C.

Example 49

3-Sulfonylamino-N-isopropylaminothiocarbonyl-4-methoxhenyl-N-2-(S)-heptylacetamide

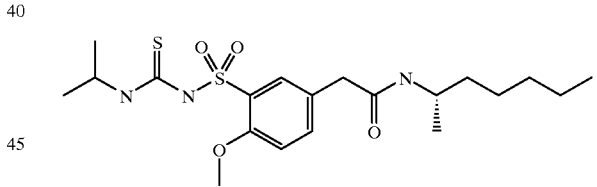

M.p.: 159° C.

Example 50

3-Sulfonylamino-N-tert-butylaminothiocarbonyl-4-methoxyphenyl-N-2-octylacetamide

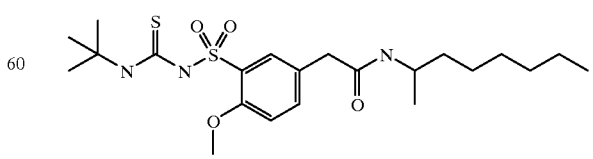

M.p.: 126° C.

Example 51

3-Sulfonylamino-N-methylaminothiocarbonyl-4-methoxhenyl-N-2-decylacetamide

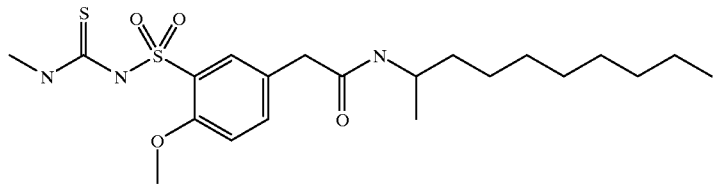

M.p.: 112° C.

Example 52

3-Sulfonylamino-N-cyclopropylaminothiocarbonyl-4-methoxyphenyl-N-2(s)-heptylacetamide

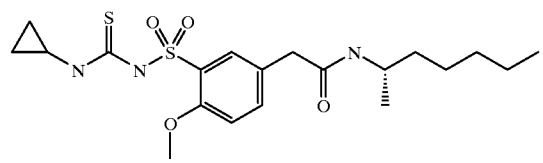

M.p.: 165° C.

Example 53

3-Sulfonylamino-N-methylaminothiocarbonyl-4-propoxyphenyl-N-2-(s)-heptylacetamide

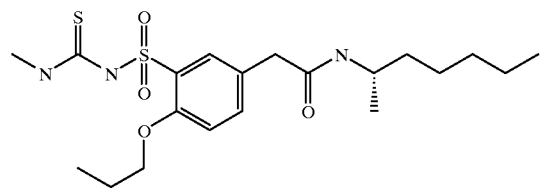

M.p.: 120° C.

Example 54

3-Sulfonylamino-N-methylaminothiocarbonyl-4-methophenyl-N-4-nonylacetamide

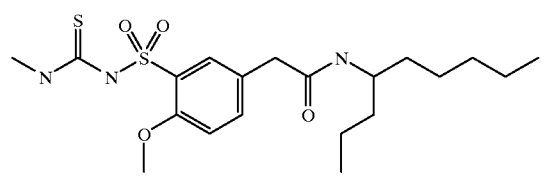

M.p.: 122° C.

Example 55

3-Sulfonylamino-N-methylaminothiocarbonyl-4-methoxyphenyl-N-4-nonyl-2-methylacetamide

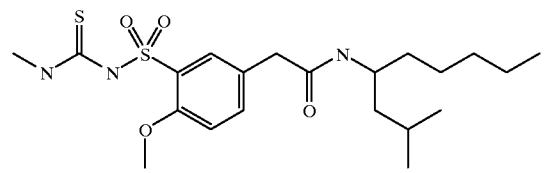

M.p.: 136° C.

Example 56

3-Sulfonylamino-N-methylaminothiocarbonyl-4-methoxyphenyl-N-4-nonyl-3-methylacetamide

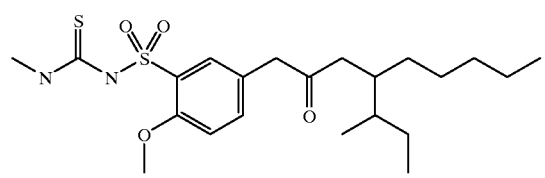

M.p.: 129° C.

Example 57

3-Sulfonylamino-N-methylaminothiocarbonyl-4-methoxyphenyl-N-3-octyl-2,2-dimethylacetamide

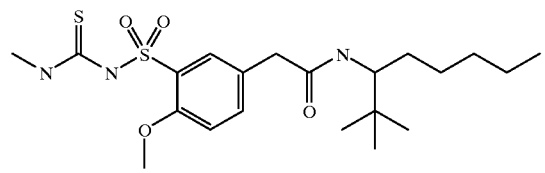

M.p.: 178° C.

Example 58

3-Sulfonylamino-N-methylaminothiocarbonyl-4-methoxyphenyl-N-3-octyl-2-methylacetamide

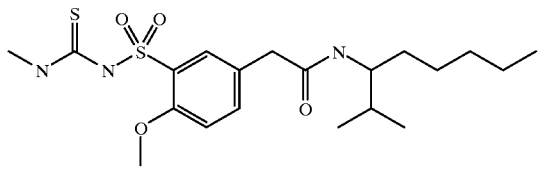

M.p.: 123° C.

Pharmacological data:

The therapeutic properties of the compounds I can be revealed using the following models:

(1) Action potential duration on the papillary muscle of the guinea-pig:

ATP deficiency states, as are observed during ischemia in the cardiac muscle cell, lead to a reduction of the action potential duration. They count as one of the causes of so-called reentry arrhythmias, which can cause sudden heart death. The opening of ATP-sensitive K channels as a result of the fall of ATP counts as causal here.

To measure the action potential, a standard microelectrode technique was employed. For this, guinea-pigs of both sexes were killed by a blow to the head, the hearts were removed, and the papillary muscles were separated out and suspended in an organ bath. The organ bath was irrigated with Ringer solution (0.9% NaCl, 0.048% KCl, 0.024% $CaCl_2$, 0.02% $NaHCO_3$ and 0.1% glucose) and aerated with a mixture of 95% oxygen and 5% carbon dioxide at a temperature of 36° C. The muscle was stimulated by means of an electrode using square-wave impulses of 1 V and 1 ms duration and a frequency of 2 Hz. The action potential was derived and recorded by means of a glass microelectrode inserted intracellularly, which was filled with 3 mM KCl solution. The substances to be tested were added to the Ringer solution in a concentration of $2.2-10^{-5}$ mol per liter. The action potential was amplified using an amplifier from Hugo Sachs and shown on an oscilloscope. The duration of the action potential was determined at a degree of repolarization of 95% (APD95). Action potential reductions were produced either by addition of a 1 μM-strength solution of the potassium channel opener Hoe 234 (J. Kaiser, H. G ögelein, Naunyn-Schmiedebergs Arch. Pharm. 1991, 343, R 59) or by addition of 2-deoxyglucose. The action potential-reducing effect of these substances was prevented or reduced by the simultaneous addition of the test substances. Test substances were added to the bath solution as stock solutions in propanediol. The values indicated relate to measurements 30 minutes after addition. Glibenclamide was used in these measurements as a standard. The test concentration in all cases is $2 \times 10^{-5}$ M.

The following values were measured:

| Example No. | APD95-start [ms] | APD95-30 min [ms] |
|---|---|---|
| 1 | 150 ± 21 | 157 ± 11 |

We claim:

1. A benzenesulfonylurea of the formula I

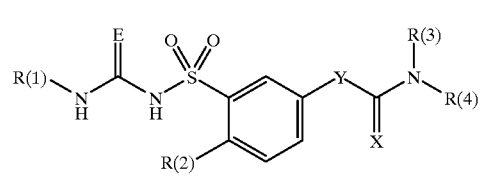

in which:

R(1) is hydrogen, alkyl having 1, 2, 3, 4, 5, 6 or 7 carbon atoms or cycloalkyl having 3, 4, 5, 6 or 7 carbon atoms;

R(2) is hydrogen, fluorine, chlorine, alkyl having 1, 2, 3, 4, 5 or 6 carbon atoms, alkoxy having 1, 2, 3, 4, 5 or 6 carbon atoms, fluoroalkoxy having 1, 2, 3, 4, 5 or 6 carbon atoms, mercaptoalkyl having 1, 2, 3, 4, 5 or 6 carbon atoms, cycloalkyl having 3, 4, 5 or 6 carbon atoms, or a $(C_1-C_8)$ chain in which one or more $CH_2$ groups can be replaced by O, NH or S;

R(3) is H, alkyl having 1, 2, 3, 4, 5, 6, 7, 8, 9, 10, 11 or 12 carbon atoms, cycloalkyl having 3, 4, 5, 6, 7, 8, 9 or 10 carbon atoms, fluoroalkyl having 1, 2, 3, 4, 5 or 6 carbon atoms, fluorocycloalkyl having 3, 4, 5 or 6 carbon atoms, or a $(C_1-C_{10})$ chain in which one or more $CH_2$ groups can be replaced by O, NH or S;

R(4) is hydrogen, alkyl having 1, 2, 3, 4, 5, 6, 7, 8, 9, 10, 11 or 12 carbon atoms, cycloalkyl having 3, 4, 5, 6, 7, 8, 9 or 10 carbon atoms, fluoroalkyl having 1, 2, 3, 4, 5 or 6 carbon atoms, fluorocycloalkyl having 3, 4, 5, or 6 carbon atoms, or a $(C_1-C_{10})$ chain in which one or more $CH_2$ can be replaced by O, NH or S; or R(3) and R(4) together form a $(CH_2)_{2-8}$ ring, in which one or more of the $CH_2$ groups can be replaced by heteroatoms;

E is oxygen;

X is oxygen or sulfur;

Y is $[CR(5)R(5')]_m$;

R(5) and R(5') independently of one another are hydrogen or alkyl having 1 or 2 carbon atoms; where the members $[CR(5)R(5')]$ are identical or different;

m is 1, 2, 3, or 4;

or a pharmaceutically acceptable salt thereof.

2. A compound of the formula I or a pharmaceutically acceptable salt thereof as claimed in claim 1, wherein:

R(1) is hydrogen, alkyl having 1, 2, 3, 4, 5, 6 or 7 carbon atoms or cycloalkyl having 3, 4, 5, 6 or 7 carbon atoms;

R(2) is hydrogen, F, Cl, alkyl having 1, 2, 3, 4, 5 or 6 carbon atoms, alkoxy having 1, 2, 3, 4, 5 or 6 carbon atoms, fluoroalkoxy having 1, 2, 3, 4, 5 or 6 carbon atoms, mercaptoalkyl having 1, 2, 3, 4, 5 or 6 carbon atoms, cycloalkyl having 3, 4, 5 or 6 carbon atoms, or a $(C_2-C_7)$ chain in which one to four $CH_2$ groups can be replaced by O, NH or S;

R(3) and R(4) are identical or different and are hydrogen, alkyl having 1, 2, 3, 4, 5, 6, 7, 8, 9, 10, 11 or 12 carbon atoms, cycloalkyl having 3, 4, 5, 6, 7, 8, 9 or 10 carbon atoms, fluoroalkyl having 1, 2, 3, 4, 5 or 6 carbon atoms, fluorocycloalkyl having 3, 4, 5 or 6 carbon atoms, or a $(C_1-C_{10})$ chain in which one to four $CH_2$ groups can be replaced by O, S or NH; or R(3) and R(4) together are $(CH_2)_{2-8}$, in which one of the $CH_2$ groups can be replaced by a O, S or NH;

E is oxygen;

X is oxygen or sulfur;

Y is $[CR(5)R(5')]_m$;

R(5) and R(5') independently of one another are hydrogen or alkyl having 1 or 2 carbon atoms; where the members [CR(5)R(5')] are identical or different;

m is 1, 2, 3 or 4.

3. A compound of the formula I or a pharmaceutically acceptable salt thereof as claimed in claim 1, wherein:

R(1) is hydrogen, alkyl having 1, 2, 3 or 4 carbon atoms or cycloalkyl having 3, 4, 5, 6 or 7 carbon atoms;

R(2) is F, Cl, alkyl having 1, 2, 3 or 4 carbon atoms, alkoxy having 1, 2, 3 or 4 carbon atoms or a ($C_2$–$C_7$) chain, in which one or more of the $CH_2$ groups can be replaced by O, S or NH;

R(3) and R(4) are identical or different and are hydrogen, alkyl having 1, 2, 3, 4, 5, 6, 7, 8, 9 or 10 carbon atoms, cycloalkyl having 3, 4, 5 or 6 carbon atoms, or a ($C_1$–$C_{10}$) chain, in which one or more $CH_2$ groups can be replaced by O, S or NH; or R(3) and R(4) are together $(CH_2)_{2-7}$, in which one of the $CH_2$ groups can be replaced by O, S or NH;

E is oxygen;

X is oxygen or sulphur;

Y is $[CR(5)R(5')]_m$;

R(5) and R(5') independently of one another are hydrogen or alkyl having 1 or 2 carbon atoms; where the members [CR(5)R(5')] are identical or different;

m is 1, 2, 3 or 4.

4. A compound of the formula I or a pharmaceutically acceptable salt thereof as claimed in claim 1, wherein:

R(1) is hydrogen, alkyl having 1, 2, 3 or 4 carbon atoms, or cycloalkyl having 3 or 4 carbon atoms;

R(2) is methoxy or ethoxy;

R(3) and R(4) are identical or different and are hydrogen, alkyl having 4, 5, 6, 7 or 8 carbon atoms, cycloalkyl having 3, 4, 5 or 6 carbon atoms or a ($C_3$–$C_8$) chain, in which one or more $CH_2$ groups can be replaced by O, S or NH; or R(3) and R(4) together are $(CH_2)_{2-8}$, in which one of the $CH_2$ groups can be replaced by O, S or NH;

E is oxygen;

X is oxygen;

Y is $[CR(5)R(5')]_m$;

R(5) and R(5') independently of one another are hydrogen or alkyl having 1 or 2 carbon atoms; where the members [CR(5)R(5')] are identical or different;

m is 1 or 2.

5. A compound of the formula I or a pharmaceutically acceptable salt thereof as claimed in claim 1, wherein:

R(1) is hydrogen, alkyl having 1, 2 or 3 carbon atoms or cycloalkyl having 3 carbon atoms;

R(2) is methoxy or ethoxy;

R(3) and R(4) are identical or different and are hydrogen, alkyl having 5, 6, 7 or 8 carbon atoms, cycloalkyl having 5 or 6 carbon atoms or a ($C_5$–$C_8$) chain, in which one or more $CH_2$groups can be replaced by O, S or NH; or R(3) and R(4) together are $(CH_2)_{5-8}$, in which one of the $CH_2$ groups can be replaced by O, S or NH;

E is oxygen;

X is oxygen;

Y is $[CR(5)R(5')]_m$;

R(5) and R(5') independently of one another are hydrogen or alkyl having 1 or 2 carbon atoms; where the members [CR(5)R(5')] are identical or different;

m is 1 or 2.

6. A compound of the formula I or a pharmaceutically acceptable salt thereof as claimed in claim 1, wherein:

R(1) is hydrogen, alkyl having 1, 2 or 3 carbon atoms or cycloalkyl having 3 carbon atoms;

R(2) is methoxy or ethoxy;

R(3) is hydrogen;

R(4) is alkyl having 5, 6, 7 or 8 carbon atoms, cycloalkyl having 5 or 6 carbon atoms or a ($C_5$–$C_8$) chain, in which one or more $CH_2$ groups can be replaced by O, S or NH;

E is oxygen;

X is oxygen;

Y is $[CR(5)R(5')]_m$;

R(5) and R(5') independently of one another are hydrogen or methyl; where the members [CR(5)R(5')] are identical or different;

m is 1 or 2.

7. A process for the preparation of a compound of the formula I as claimed in claim 1, which comprises (a) reacting a sulfonamide of the formula II

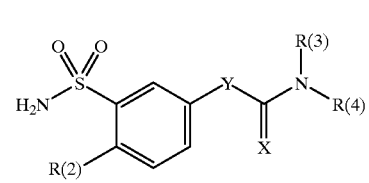

or its salt of the formula III

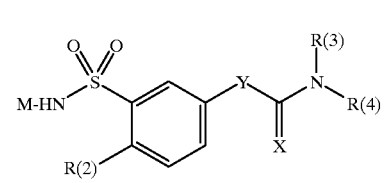

in which M is a cation selected from the group consisting of alkali metal cations and alkaline earth metal cations, R(2), R(3), R(4), X and Y have the meanings indicated in claim 1, with an R(1)-substituted isocyanate of the formula IV

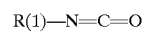  IV in which R(1) has the meaning indicated in claim 1, to form a substituted benzenesulfonylurea of the formula I; or (b) reacting an aromatic benzenesulfonamide of the formula II or its salt of the formula III with an R(1)-substituted trichloroacetamide of the formula V

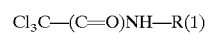

in the presence of a base to form a benzenesulfonylurea of the formula I; or (c) reacting an amine of the formula R(1)—$NH_2$ with a benzenesulfonyl isocyanate of the formula VII

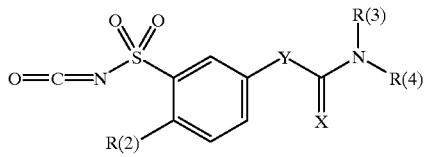

VII to form a benzenesulfonylurea of the formula I; or
(d) reacting a benzenesulfonylurea of the formula IX

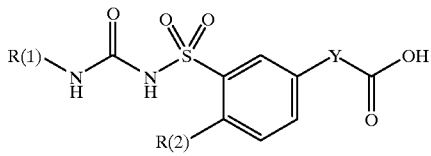

IX and R(3)R(4)NH in the presence of a dehydrating agent or after activation by means of a carbonyl halide or formation of a mixed anhydride to form a benzenesulfonylurea of the formula I.

8. A pharmaceutical composition comprising a benzenesulfonylurea of the formula I or a pharmaceutically acceptable salt thereof as claimed in claim 1, together with a pharmaceutically acceptable carrier.

9. A process for the preparation of a compound of the formula Ia

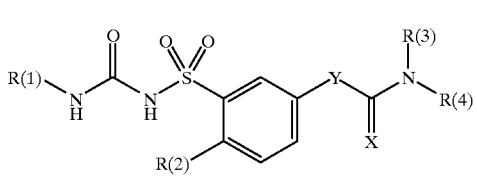

Ia in which:
R(1) is hydrogen, alkyl having 1, 2, 3, 4, 5, 6 or 7 carbon atoms or cycloalkyl having 3, 4, 5, 6 or 7 carbon atoms;
R(2) is hydrogen, fluorine, chlorine, alkyl having 1, 2, 3, 4, 5 or 6 carbon atoms, alkoxy having 1, 2, 3, 4, 5 or 6 carbon atoms, fluoroalkoxy having 1, 2, 3, 4, 5 or 6 carbon atoms, mercaptoalkyl having 1, 2, 3, 4, 5 or 6 carbon atoms, cycloalkyl having 3, 4, 5 or 6 carbon atoms, or a ($C_1$–$C_8$) chain in which one or more $CH_2$ groups can be replaced by O, NH or S;
R(3) is H, alkyl having 1, 2, 3, 4, 5, 6, 7, 8, 9, 10, 11 or 12 carbon atoms, cycloalkyl having 3, 4, 5, 6, 7, 8, 9 or 10 carbon atoms, fluoroalkyl having 1, 2, 3, 4, 5 or 6 carbon atoms, fluorocycloalkyl having 3, 4, 5 or 6 carbon atoms, or a ($C_1$–$C_{10}$) chain in which one or more $CH_2$ groups can be replaced by O, NH or S;
R(4) is hydrogen, alkyl having 1, 2, 3, 4, 5, 6, 7, 8, 9, 10, 11 or 12 carbon atoms, cycloalkyl having 3, 4, 5, 6, 7, 8, 9 or 10 carbon atoms, fluoroalkyl having 1, 2, 3, 4, 5 or 6 carbon atoms, fluorocycloalkyl having 3, 4, 5 or 6 carbon atoms, or a ($C_1$–$C_{10}$) chain in which one or more $CH_2$ groups can be replaced by O, NH or S; or
R(3) and R(4) together form a $(CH_2)_{2-8}$ ring, in which one or more of the $CH_2$ groups can be replaced by heteroatoms;
X is oxygen or sulfur;
Y is $[CR(5)R(5')]_m$
R(5) and R(5') independently of one another are hydrogen or alkyl having 1 or 2 carbon atoms; where the members [CR(5)R(5')] are identical or different;
m is 1, 2, 3 or 4;
comprising the step of desulfurizing a compound of the formula Ib

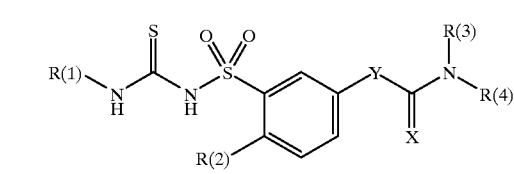

Ib

10. A process for the preparation of a compound of the formula Ia as claimed in claim 9, wherein a compound of the formula Ib is reacted with an oxide or a salt of a heavy metal.

11. A process for the preparation of a compound of the formula Ia as claimed in claim 9, wherein a compound of the formula Ib is reacted with an oxidant.

12. A process for the preparation of a compound of the formula Ia as claimed in claim 11, wherein said oxidant is selected from the group consisting of hydrogen peroxide, sodium peroxide, and nitrous acid.

13. A process for the preparation of a compound of the formula Ia as claimed in claim 9, wherein a compound of the formula Ib is reacted with phosgene or phosphorus pentachloride and then hydrolyzed to form said compound of the formula Ia.

14. A method of investigating the inhibition of ATP-sensitive potassium channels, comprising administering an effective amount of a benzenesulfonylurea or benzenesulfonylthiourea of the formula I

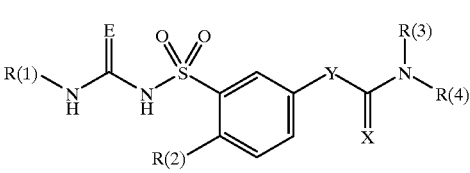

I in which:
R(1) is hydrogen, alkyl having 1, 2, 3, 4, 5, 6 or 7 carbon atoms or cycloalkyl having 3, 4, 5, 6 or 7 carbon atoms;
R(2) is hydrogen, fluorine, chlorine, alkyl having 1, 2, 3, 4, 5 or 6 carbon atoms, alkoxy having 1, 2, 3, 4, 5 or 6 carbon atoms, fluoroalkoxy having 1, 2, 3, 4, 5 or 6 carbon atoms, mercaptoalkyl having 1, 2, 3, 4, 5 or 6 carbon atoms, cycloalkyl having 3, 4, 5 or 6 carbon atoms, or a ($C_1$–$C_8$) chain in which one or more $CH_2$ groups can be replaced by O, NH or S;
R(3) is H, alkyl having 1, 2, 3, 4, 5, 6, 7, 8, 9, 10, 11 or 12 carbon atoms, cycloalkyl having 3, 4, 5, 6, 7, 8, 9 or 10 carbon atoms, fluoroalkyl having 1, 2, 3, 4, 5 or 6 carbon atoms, fluorocycloalkyl having 3, 4, 5 or 6 carbon atoms, or a ($C_1$–$C_{10}$) chain in which one or more $CH_2$ groups can be replaced by O, NH or S;
R(4) is hydrogen, alkyl having 1, 2, 3, 4, 5, 6, 7, 8, 9, 10, 11 or 12 carbon atoms, cycloalkyl having 3, 4, 5, 6, 7, 8, 9 or 10 carbon atoms, fluoroalkyl having 1, 2, 3, 4, 5 or 6 carbon atoms, fluorocycloalkyl having 3, 4, 5, or 6 carbon atoms, or a ($C_1$–$C_{10}$) chain in which one or more $CH_2$ can be replaced by O, NH or S; or R(3) and R(4) together form a $(CH_2)_{2-8}$ ring, in which one or more of the $CH_2$ groups can be replaced by heteroatoms;

E is oxygen;

X is oxygen or sulfur;

Y is $[CR(5)R(5')]_m$;

R(5) and R(5') independently of one another are hydrogen or alkyl having 1 or 2 carbon atoms; where the members $[CR(5)R(5')]$ are identical or different;

m is 1, 2, 3, or 4;

or a pharmaceutically acceptable salt thereof as a diagnostic agent.

* * * * *